(12) United States Patent
Rensing et al.

(10) Patent No.: US 8,280,651 B2
(45) Date of Patent: Oct. 2, 2012

(54) METER ELECTRONICS AND METHODS FOR VERIFICATION DIAGNOSTICS FOR A FLOW METER

(75) Inventors: Matthew Joseph Rensing, Cincinnati, OH (US); Andrew Timothy Patten, Boulder, CO (US); Timothy J. Cunningham, Boulder, CO (US); Mark James Bell, Longmont, CO (US)

(73) Assignee: Micro Motion, Inc., Boulder, CO (US)

( * ) Notice: Subject to any disclaimer, the term of this patent is extended or adjusted under 35 U.S.C. 154(b) by 0 days.

(21) Appl. No.: 12/948,141

(22) Filed: Nov. 17, 2010

(65) Prior Publication Data
US 2011/0178738 A1 Jul. 21, 2011

Related U.S. Application Data

(62) Division of application No. 12/066,434, filed as application No. PCT/US2005/033285 on Sep. 19, 2005, now Pat. No. 7,865,318.

(51) Int. Cl.
*G01N 11/00* (2006.01)
(52) U.S. Cl. .......................................... 702/56
(58) Field of Classification Search ...................... 702/56
See application file for complete search history.

(56) References Cited

U.S. PATENT DOCUMENTS

| | | | |
|---|---|---|---|
| 4,920,787 A | 5/1990 | Dual et al. | |
| 5,579,243 A * | 11/1996 | Levine | 708/300 |
| 5,926,096 A * | 7/1999 | Mattar et al. | 340/606 |
| 6,092,409 A | 7/2000 | Patten et al. | |
| 6,347,293 B1 | 2/2002 | Cunningham et al. | |
| 6,360,579 B1 | 3/2002 | De Boom et al. | |
| 6,678,624 B2 | 1/2004 | Normen | |
| 6,782,333 B2 | 8/2004 | Baker et al. | |
| 7,716,995 B2 * | 5/2010 | Patten et al. | 73/861.355 |
| 7,774,150 B2 * | 8/2010 | Stack | 702/54 |
| 7,865,318 B2 * | 1/2011 | Rensing et al. | 702/56 |
| 2003/0191598 A1 | 10/2003 | Normen | |
| 2005/0072234 A1 * | 4/2005 | Zhu et al. | 73/579 |
| 2007/0186682 A1 * | 8/2007 | Duffill et al. | 73/861.354 |
| 2008/0184813 A1 * | 8/2008 | Patten et al. | 73/861.355 |

FOREIGN PATENT DOCUMENTS

| | | |
|---|---|---|
| EP | 0816807 A2 | 1/1998 |
| FR | 2754898 A1 | 4/1998 |
| JP | 200452516 | 2/2004 |
| RU | 2247331 C2 | 2/2005 |
| WO | 03021205 A1 | 3/2003 |
| WO | 2005040734 A1 | 5/2005 |
| WO | 2005050145 A1 | 6/2005 |
| WO | WO 2007/040468 * | 4/2007 |

* cited by examiner

*Primary Examiner* — Michael Nghiem
(74) *Attorney, Agent, or Firm* — The Ollila Law Group LLC

(57) ABSTRACT

Meter electronics (20) for a flow meter (5) is provided according to an embodiment of the invention. The meter electronics (20) includes an interface (201) for receiving a vibrational response from the flow meter (5) and a processing system (203) in communication with the interface (201). The vibrational response is a response to a vibration of the flow meter (5) at a substantially resonant frequency. The processing system (203) is configured to receive the vibrational response from the interface (201), determine a frequency ($\omega_0$) of the vibrational response, determine a response voltage (V) and a drive current (I) of the vibrational response, measure a decay characteristic ($\zeta$) of the flow meter (5), and determine the stiffness parameter (K) from the frequency ($\omega_0$), the response voltage (V), the drive current (I), and the decay characteristic ($\zeta$).

26 Claims, 12 Drawing Sheets

METER ELECTRONICS AND METHODS FOR VERIFICATION DIAGNOSTICS FOR A FLOW METER

This application is a Divisional of and claims the benefit of U.S. patent application Ser. No. 12/066,434, now U.S. Pat. No. 7,865,318, filed on Mar. 11, 2008, entitled "Meter electronics and methods for verification diagnostics for a flow meter", which hereby is incorporated by reference into this application.

BACKGROUND OF THE INVENTION

1. Field of the Invention

The present invention relates to a meter electronics and methods for verification diagnostics for a flow meter.

2. Statement of the Problem

Vibrating conduit sensors, such as Coriolis mass flow meters or vibrating tube densitometers, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness, and damping characteristics of the containing conduit and the material contained therein.

A conduit of a vibratory flow meter can include one or more flow tubes. A flow tube is forced to vibrate at a resonant frequency, where the resonant frequency of the tube is proportional to the density of the fluid in the flow tube. Sensors located on the inlet and outlet sections of the tube measure the relative vibration between the ends of the tube. During flow, the vibrating tube and the flowing mass couple together due to Coriolis forces, causing a phase shift in the vibration between the ends of the tube. The phase shift is directly proportional to the mass flow.

A typical Coriolis mass flow meter includes one or more conduits that are connected inline in a pipeline or other transport system and convey material, e.g., fluids, slurries and the like, in the system. Each conduit may be viewed as having a set of natural vibration modes including, for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation by cabling. The instrumentation receives signals from the two pickoff sensors and processes the signals in order to derive a mass flow rate measurement.

The phase difference between the two sensor signals is related to the mass flow rate of the material flowing through the flow tube or flow tubes. The mass flow rate of the material is proportional to the time delay between the two sensor signals, and the mass flow rate can therefore be determined by multiplying the time delay by a Flow Calibration Factor (FCF), where the time delay comprises a phase difference divided by frequency. The FCF reflects the material properties and cross-sectional properties of the flow tube. In the prior art, the FCF is determined by a calibration process prior to installation of the flow meter into a pipeline or other conduit. In the calibration process, a fluid is passed through the flow tube at a given flow rate and the proportion between the phase difference and the flow rate is calculated.

One advantage of a Coriolis flow meter is that the accuracy of the measured mass flow rate is not affected by wear of moving components in the flow meter. The flow rate is determined by multiplying the phase difference between two points of the flow tube and the flow calibration factor. The only input is the sinusoidal signals from the sensors, indicating the oscillation of two points on the flow tube. The phase difference is calculated from these sinusoidal signals. There are no moving components in the vibrating flow tube. Therefore, the measurement of the phase difference and the flow calibration factor are not affected by wear of moving components in the flow meter.

The FCF can be related to a stiffness characteristic of the meter assembly. If the stiffness characteristic of the meter assembly changes, then the FCF will also change. Changes therefore will affect the accuracy of the flow measurements generated by the flow meter. Changes in the material and cross-sectional properties of a flow tube can be caused by erosion or corrosion, for example. Consequently, it is highly desirable to be able to detect and/or quantify any changes to the stiffness of the meter assembly in order to maintain a high level of accuracy in the flow meter.

SUMMARY OF THE SOLUTION

Meter electronics for a flow meter is provided according to an embodiment of the invention. The meter electronics comprises an interface for receiving a vibrational response from the flow meter and a processing system in communication with the interface. The vibrational response comprises a response to a vibration of the flow meter at a substantially resonant frequency. The processing system is configured to receive the vibrational response from the interface, determine a frequency ($\omega_0$) of the vibrational response, determine a response voltage (V) and a drive current (I) of the vibrational response, measure a decay characteristic ($\zeta$) of the flow meter, and determine the stiffness parameter (K) from the frequency ($\omega_0$), the response voltage (V), the drive current (I), and the decay characteristic ($\zeta$).

A method for determining a stiffness parameter (K) of a flow meter is provided according to an embodiment of the invention. The method comprises receiving a vibrational response from the flow meter. The vibrational response comprises a response to a vibration of the flow meter at a substantially resonant frequency. The method further comprises determining a frequency ($\omega_0$) of the vibrational response, determining a response voltage (V) and a drive current (I) of the vibrational response, and measuring a decay characteristic ($\zeta$) of the flow meter. The method further comprises determining the stiffness parameter (K) from the frequency ($\omega_0$), the response voltage (V), the drive current (I), and the decay characteristic ($\zeta$).

A method for determining a stiffness change ($\Delta K$) in a flow meter is provided according to an embodiment of the invention. The method comprises receiving a vibrational response from the flow meter. The vibrational response comprises a response to a vibration of the flow meter at a substantially resonant frequency. The method further comprises determining a frequency ($\omega_0$) of the vibrational response, determining a response voltage (V) and a drive current (I) of the vibrational response, and measuring a decay characteristic (ζ) of the flow meter. The method further comprises determining the stiffness parameter (K) from the frequency ($\omega_0$), the response voltage (V), the drive current (I), and the decay characteristic (ζ). The method further comprises receiving a second vibrational response from the flow meter at a second time $t_2$, generating a second stiffness characteristic ($K_2$) from the second vibrational response, comparing the second stiffness characteristic ($K_2$) to the stiffness parameter (K), and detecting the stiffness change (ΔK) if the second stiffness characteristic ($K_2$) differs from the stiffness parameter (K) by more than a predetermined tolerance.

Meter electronics for a flow meter is provided according to an embodiment of the invention. The meter electronics comprises an interface for receiving three or more vibrational responses from the flow meter. The three or more vibrational responses include a substantially fundamental frequency response and two or more non-fundamental frequency responses. The meter electronics further comprises a processing system in communication with the interface and configured to receive the three or more vibrational responses from the interface, generate a pole-residue frequency response function from the three or more vibrational responses, and determine at least a stiffness parameter (K) from the pole-residue frequency response function.

A method for determining a stiffness parameter (K) of a flow meter is provided according to an embodiment of the invention. The method comprises receiving three or more vibrational responses. The three or more vibrational responses include a substantially fundamental frequency response and two or more non-fundamental frequency responses. The method further comprises generating a pole-residue frequency response function from the three or more vibrational responses and determining at least a stiffness parameter (K) from the pole-residue frequency response function.

A method for determining a stiffness parameter (K) of a flow meter is provided according to an embodiment of the invention. The method comprises receiving three or more vibrational responses. The three or more vibrational responses include a substantially fundamental frequency response and two or more non-fundamental frequency responses. The method further comprises generating a pole-residue frequency response function from the three or more vibrational responses and determining at least a stiffness parameter (K) from the pole-residue frequency response function. The method further comprises receiving a second set of three or more vibrational responses from the flow meter at a second time $t_2$, generating a second stiffness characteristic ($K_2$) from the second set of three or more vibrational responses, comparing the second stiffness characteristic ($K_2$) to the stiffness parameter (K), and detecting the stiffness change (ΔK) if the second stiffness characteristic ($K_2$) differs from the stiffness parameter (K) by more than a predetermined tolerance.

ASPECTS OF THE INVENTION

In one aspect of the meter electronics, measuring the decay characteristic (ζ) further comprises allowing the vibrational response of the flow meter to decay down to a predetermined vibrational target.

In another aspect of the meter electronics, the processing system is further configured to measure the decay characteristic (ζ) by removing the excitation of the flow meter and allowing the vibrational response of the flow meter to decay down to a predetermined vibrational target while measuring the decay characteristic.

In another aspect of the meter electronics, the stiffness parameter (K) comprises $K=(I*BL_{PO}*BL_{DR}*\omega_0)/2\zeta V$.

In one aspect of the method, measuring the decay characteristic (ζ) further comprises allowing the vibrational response of the flow meter to decay down to a predetermined vibrational target.

In another aspect of the method, measuring the decay characteristic (ζ) further comprises removing the excitation of the flow meter and allowing the vibrational response of the flow meter to decay down to a predetermined vibrational target while measuring the decay characteristic.

In yet another aspect of the method, the stiffness parameter (K) comprising $K=(I*BL_{PO}*BL_{DR}*\omega_0)/2\zeta V$.

In yet another aspect of the method, generating the second stiffness characteristic ($K_2$) from the second vibrational response comprises generating the second stiffness characteristic ($K_2$) from a second frequency, a second response voltage, a second drive current, and a second damping characteristic.

In yet another aspect of the method, the method further comprises detecting the stiffness change (ΔK) if the second stiffness characteristic ($K_2$) differs from the stiffness parameter (K) by more than a predetermined stiffness tolerance.

In yet another aspect of the method, the method further comprises quantifying the stiffness change (ΔK) from the comparing of K and $K_2$.

In one embodiment of the meter electronics, the processing system is further configured to determine a damping parameter (C) from the pole-residue frequency response function.

In another embodiment of the meter electronics, the processing system is further configured to determine a mass parameter (M) from the pole-residue frequency response function.

In yet another embodiment of the meter electronics, the processing system is further configured to compute a pole (λ), a left residue ($R_L$), and a right residue ($R_R$) from the pole-residue frequency response function.

In yet another embodiment of the meter electronics, the three or more vibrational responses comprise at least one tone above the fundamental frequency response and at least one tone below the fundamental frequency response.

In yet another embodiment of the meter electronics, the three or more vibrational responses comprise at least two tones above the fundamental frequency response and at least two tones below the fundamental frequency response.

In yet another embodiment of the meter electronics, the pole-residue frequency response function comprises a first order pole-residue frequency response function.

In yet another embodiment of the meter electronics, the pole-residue frequency response function comprises a first order pole-residue frequency response function that comprises $H(\omega)=R/(j\omega-\lambda)+\overline{R}/(j\omega-\overline{\lambda})$.

In yet another embodiment of the meter electronics, the pole-residue frequency response function comprises a first order pole-residue frequency response function that comprises $H(\omega)=R/(j\omega-\lambda)+\overline{R}/(j\omega-\overline{\lambda})$ and wherein the stiffness parameter (K), the damping parameter (C), and the mass parameter (M) are determined according to the equations $M=\frac{1}{2}jR\omega_d$, $K=(\omega_n)^2M$, and $C=2\zeta\omega_nM$.

In yet another embodiment of the meter electronics, the pole-residue frequency response function comprises a second order pole-residue frequency response function.

In yet another embodiment of the meter electronics, the pole-residue frequency response function comprises a second order pole-residue frequency response function that comprises $$\dot{H}(\omega) = \frac{\dot{X}(\omega)}{F(\omega)} = \frac{j\omega}{-M\omega^2 + jC\omega + K}.$$

In yet another embodiment of the meter electronics, the pole-residue frequency response function comprises a second order pole-residue frequency response function that comprises $$\dot{H}(\omega) = \frac{\dot{X}(\omega)}{F(\omega)} = \frac{j\omega}{-M\omega^2 + jC\omega + K}$$

and wherein the stiffness parameter (K) is determined according to $K=((\omega_n)^2\omega \text{Im}[\dot{H}(\omega)])/((\omega_n)^2-\omega^2)|\dot{H}(\omega)|^2)$, the mass parameter (M) is determined according to $M=K/(\omega_n)^2$, and the damping parameter (C) is determined according to $C=\text{Re}[\dot{H}(\omega)]/|\dot{H}(\omega)|^2$.

In one embodiment of the method, the determining comprises further determining a damping parameter (C) from the pole-residue frequency response function.

In another embodiment of the method, the determining comprises further determining a mass parameter (M) from the pole-residue frequency response function.

In yet another embodiment of the method, the determining further comprises computing a pole ($\lambda$), a left residue ($R_L$), and a right residue ($R_R$) from the pole-residue frequency response function.

In yet another embodiment of the method, the three or more vibrational responses comprise at least one tone above the fundamental frequency response and at least one tone below the fundamental frequency response.

In yet another embodiment of the method, the three or more vibrational responses comprise at least two tones above the fundamental frequency response and at least two tones below the fundamental frequency response.

In yet another embodiment of the method, the pole-residue frequency response function comprises a first order pole-residue frequency response function.

In yet another embodiment of the method, the pole-residue frequency response function comprises a first order pole-residue frequency response function comprising $H(\omega)=R/(j\omega-\lambda)+\overline{R}/(j\omega-\overline{\lambda})$.

In yet another embodiment of the method, the pole-residue frequency response function comprises a first order pole-residue frequency response function comprising $H(\omega)=R/(j\omega-\lambda)+\overline{R}/(j\omega-\overline{\lambda})$ and wherein the stiffness parameter (K), the damping parameter (C), and the mass parameter (M) are determined according to the equations $M=\frac{1}{2}jR\omega_d$, $K=(\omega_n)^2 M$, and $C=2\zeta\omega_n M$.

In yet another embodiment of the method, the pole-residue frequency response function comprises a second order pole-residue frequency response function.

In yet another embodiment of the method, the pole-residue frequency response function comprises a second order pole-residue frequency response function comprising $$\dot{H}(\omega) = \frac{\dot{X}(\omega)}{F(\omega)} = \frac{j\omega}{-M\omega^2 + jC\omega + K}.$$

In yet another embodiment of the method, the pole-residue frequency response function comprises a second order pole-residue frequency response function that comprises $$\dot{H}(\omega) = \frac{\dot{X}(\omega)}{F(\omega)} = \frac{j\omega}{-M\omega^2 + jC\omega + K}$$

and wherein the stiffness parameter (K) is determined according to $K=((\omega_n)^2\omega \text{Im}[\dot{H}(\omega)])/((\omega_n)^2-\omega^2)|\dot{H}(\omega)|^2)$, the mass parameter (M) is determined according to $M=K/(\omega_n)^2$, and the damping parameter (C) is determined according to $C=\text{Re}[\dot{H}(\omega)]/|\dot{H}(\omega)|^2$.

In yet another embodiment of the method, the method further comprises detecting the stiffness change ($\Delta K$) if the second stiffness characteristic ($K_2$) differs from the stiffness parameter (K) by more than a predetermined stiffness tolerance.

In yet another embodiment of the method, the method further comprises quantifying the stiffness change ($\Delta K$) from the comparing of K and $K_2$.

DESCRIPTION OF THE DRAWINGS

The same reference number represents the same element on all drawings.

DETAILED DESCRIPTION OF THE INVENTION

FIGS. 1-12 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
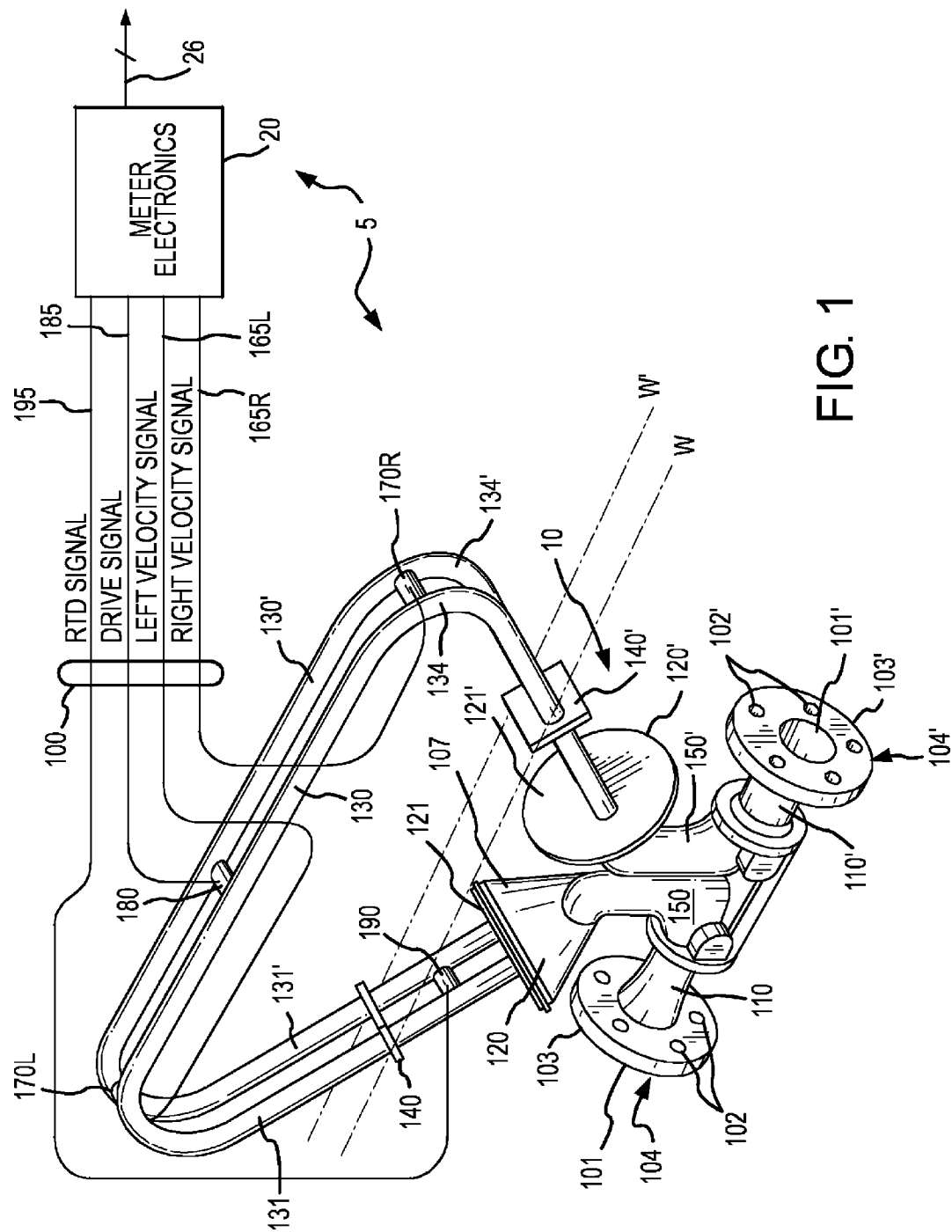
FIG. 1 shows a flow meter comprising a meter assembly and meter electronics.

FIG. 1 shows a flow meter 5 comprising a meter assembly 10 and meter electronics 20. Meter assembly 10 responds to mass flow rate and density of a process material. Meter electronics 20 is connected to meter assembly 10 via leads 100 to provide density, mass flow rate, and temperature information over path 26, as well as other information not relevant to the present invention. A Coriolis flow meter structure is described although it is apparent to those skilled in the art that the present invention could be practiced as a vibrating tube densitometer without the additional measurement capability provided by a Coriolis mass flow meter.

Meter assembly 10 includes a pair of manifolds 150 and 150', flanges 103 and 103' having flange necks 110 and 110', a pair of parallel flow tubes 130 and 130', drive mechanism 180, temperature sensor 190, and a pair of velocity sensors 170L and 170R. Flow tubes 130 and 130' have two essentially straight inlet legs 131 and 131' and outlet legs 134 and 134' which converge towards each other at flow tube mounting blocks 120 and 120'. Flow tubes 130 and 130' bend at two symmetrical locations along their length and are essentially parallel throughout their length. Brace bars 140 and 140' serve to define the axis W and W' about which each flow tube oscillates.

The side legs 131, 131' and 134, 134' of flow tubes 130 and 130' are fixedly attached to flow tube mounting blocks 120 and 120' and these blocks, in turn, are fixedly attached to manifolds 150 and 150'. This provides a continuous closed material path through Coriolis meter assembly 10.

When flanges 103 and 103', having holes 102 and 102' are connected, via inlet end 104 and outlet end 104' into a process line (not shown) which carries the process material that is being measured, material enters end 104 of the meter through an orifice 101 in flange 103 is conducted through manifold 150 to flow tube mounting block 120 having a surface 121. Within manifold 150 the material is divided and routed through flow tubes 130 and 130'. Upon exiting flow tubes 130 and 130', the process material is recombined in a single stream within manifold 150' and is thereafter routed to exit end 104' connected by flange 103' having bolt holes 102' to the process line (not shown).

Flow tubes 130 and 130' are selected and appropriately mounted to the flow tube mounting blocks 120 and 120' so as to have substantially the same mass distribution, moments of inertia and Young's modulus about bending axes W-W and W'-W', respectively. These bending axes go through brace bars 140 and 140'. Inasmuch as the Young's modulus of the flow tubes change with temperature, and this change affects the calculation of flow and density, resistive temperature detector (RTD) 190 is mounted to flow tube 130', to continuously measure the temperature of the flow tube. The temperature of the flow tube and hence the voltage appearing across the RTD for a given current passing therethrough is governed by the temperature of the material passing through the flow tube. The temperature dependent voltage appearing across the RTD is used in a well known method by meter electronics 20 to compensate for the change in elastic modulus of flow tubes 130 and 130' due to any changes in flow tube temperature. The RTD is connected to meter electronics 20 by lead 195.

Both flow tubes 130 and 130' are driven by driver 180 in opposite directions about their respective bending axes W and W' and at what is termed the first out-of-phase bending mode of the flow meter. This drive mechanism 180 may comprise any one of many well known arrangements, such as a magnet mounted to flow tube 130' and an opposing coil mounted to flow tube 130 and through which an alternating current is passed for vibrating both flow tubes. A suitable drive signal is applied by meter electronics 20, via lead 185, to drive mechanism 180.

Meter electronics 20 receives the RTD temperature signal on lead 195, and the left and right velocity signals appearing on leads 165L and 165R, respectively. Meter electronics 20 produces the drive signal appearing on lead 185 to drive element 180 and vibrate tubes 130 and 130'. Meter electronics 20 processes the left and right velocity signals and the RTD signal to compute the mass flow rate and the density of the material passing through meter assembly 10. This information, along with other information, is applied by meter electronics 20 over path 26 to utilization means 29.

Figure 2:
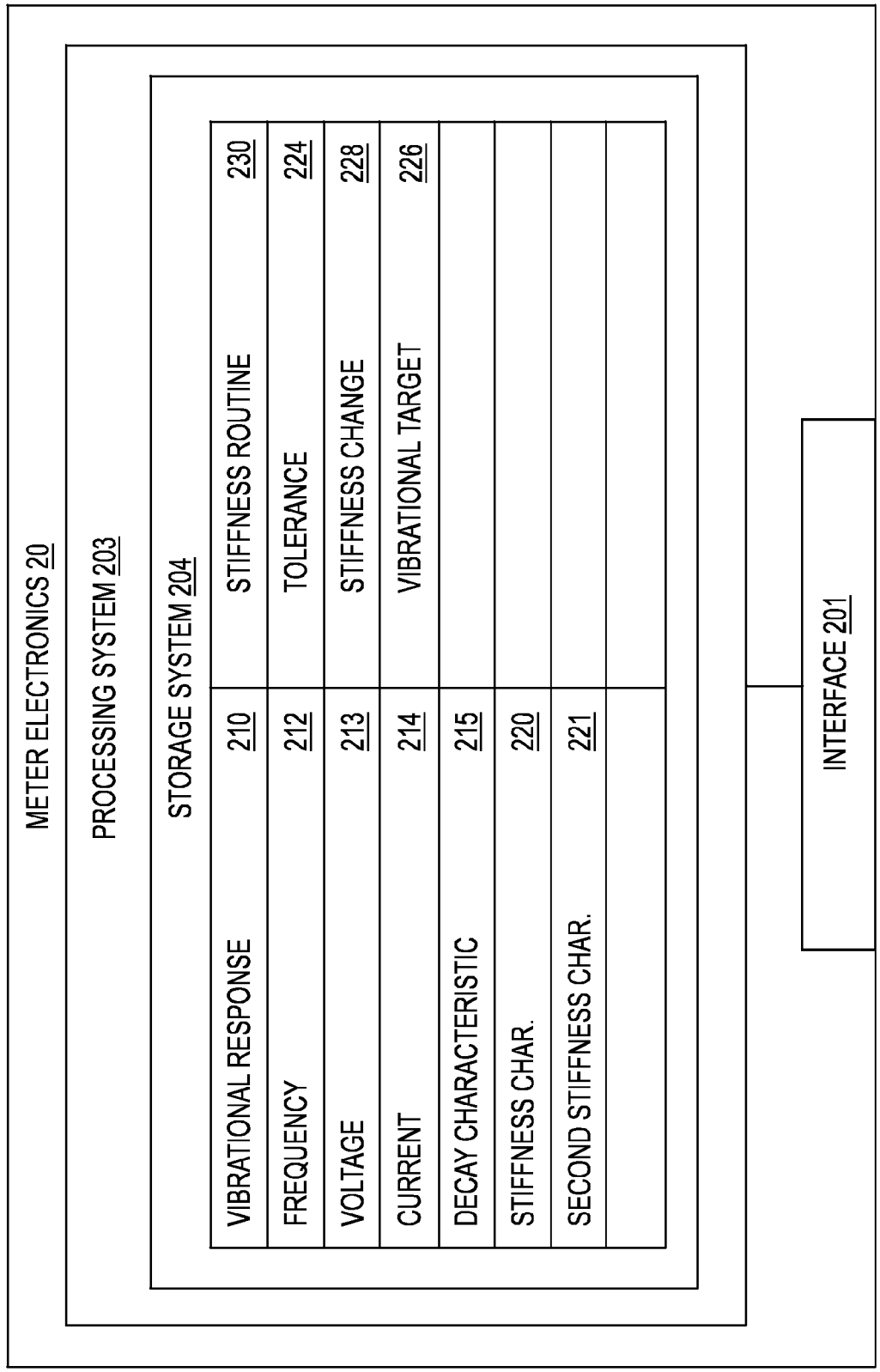
FIG. 2 shows meter electronics according to an embodiment of the invention.

FIG. 2 shows the meter electronics 20 according to an embodiment of the invention. The meter electronics 20 can include an interface 201 and a processing system 203. The meter electronics 20 receives a vibrational response 210, such as from the meter assembly 10, for example. The meter electronics 20 processes the vibrational response 210 in order to obtain flow characteristics of the flow material flowing through the meter assembly 10. In addition, in the meter electronics 20 according to the invention, the vibrational response 210 is also processed in order to determine a stiffness parameter (K) of the meter assembly 10. Furthermore, the meter electronics 20 can process two or more such vibrational responses, over time, in order to detect a stiffness change (ΔK) in the meter assembly 10. The stiffness determination can be made under flow or no-flow conditions. A no-flow determination may offer the benefit of a reduced noise level in the resulting vibrational response.

As previously discussed, the Flow Calibration Factor (FCF) reflects the material properties and cross-sectional properties of the flow tube. A mass flow rate of flow material flowing through the flow meter is determined by multiplying a measured time delay (or phase difference/frequency) by the FCF. The FCF can be related to a stiffness characteristic of the meter assembly. If the stiffness characteristic of the meter assembly changes, then the FCF will also change. Changes in the stiffness of the flow meter therefore will affect the accuracy of the flow measurements generated by the flow meter.

The invention is significant because it enables the meter electronics 20 to perform a stiffness determination in the field, without performing an actual flow calibration test. It enables a stiffness determination without a calibration test stand or other special equipment or special fluids. This is desirable because performing a flow calibration in the field is expensive, difficult, and time-consuming. However, a better and easier calibration check is desirable because the stiffness of the meter assembly 10 can change over time, in use. Such changes can be due to factors such as erosion of a flow tube, corrosion of a flow tube, and damage to the meter assembly 10, for example.

The invention can be illustrated with a mathematical model. The vibrational response of a flow meter can be represented by an open loop, second order drive model, comprising:

$$M\ddot{x}+C\dot{x}+Kx=f \quad (1)$$

where f is the force applied to the system, M is a mass of the system, C is a damping characteristic, and K is a stiffness characteristic of the system. The term K comprises $K=M(\omega_0)^2$ and the term C comprises $C=M2\zeta\omega_0$, where comprises a decay characteristic, and $\omega_0=2\pi f_0$ where $f_0$ is the natural/resonant frequency of the meter assembly 10 in Hertz. In addition, x is the physical displacement distance of the vibration, $\dot{x}$ is the velocity of the flowtube displacement, and $\ddot{x}$ is the acceleration. This is commonly referred to as the MCK model. This formula can be rearranged into the form:

$$M[s^2+2\zeta\omega_0 s+\omega_0^2]x=f \quad (2)$$

Equation (2) can be further manipulated into a transfer function form. In the transfer function form, a term of displacement over force is used, comprising:

$$\frac{x}{f} = \frac{s}{M[s^2 + 2\zeta\omega_0 s + \omega_0^2]} \quad (3)$$

Well-know magnetic equations can be used to simplify equation (3). Two applicable equations are:

$$V=BL_{PO}*\dot{x} \quad (4)$$

and $$f=BL_{DR}*I \quad (5)$$

The sensor voltage $V_{EMF}$ of equation (4) (at a pick-off sensor 170L or 170R) is equal to the pick-off sensitivity factor $BL_{PO}$ multiplied by the pick-off velocity of motion $\dot{x}$. The pick-off sensitivity factor $BL_{PO}$ is generally known or measured for each pick-off sensor. The force (f) generated by the driver 180 of equation (5) is equal to the driver sensitivity factor $BL_{DR}$ multiplied by the drive current (I) supplied to the driver 180. The driver sensitivity factor $BL_{DR}$ of the driver 180 is generally known or measured. The factors $BL_{PO}$ and $BL_{DR}$ are both a function of temperature, and can be corrected by a temperature measurement.

By substituting the magnetic equations (4) and (5) into the transfer function of equation (3), the result is:

$$\frac{V}{I} = \frac{BL_{PO}*BL_{DR}*s}{M[s^2 + 2\zeta\omega_0 s + \omega_0^2]} \quad (6)$$

If the meter assembly 10 is driven open loop on resonance, i.e., at a resonant/natural frequency $\omega_0$ (where $\omega_0=2\pi f_0$), then equation (6) can be rewritten as:

$$\left(\frac{V}{I}\right)_{\omega_0} = \frac{BL_{PO}*BL_{DR}*\omega_0}{2\zeta[M\omega_0^2]} \quad (7)$$

By substituting for stiffness, equation (7) is simplified to:

$$\left(\frac{V}{I}\right)_{\omega_0} = \frac{BL_{PO}*BL_{DR}*\omega_0}{2\zeta K} \quad (8)$$

Here, the stiffness parameter (K) can be isolated in order to obtain:

$$K = \frac{I*BL_{PO}*BL_{DR}*\omega_0}{2\zeta V} \quad (9)$$

As a consequence, by measuring/quantifying the decay characteristic ($\zeta$), along with the drive voltage (V) and drive current (I), the stiffness parameter (K) can be determined. The response voltage (V) from the pick-offs can be determined from the vibrational response, along with the drive current (I). The process of determining the stiffness parameter (K) is discussed in more detail in conjunction with FIG. 3, below.

In use, the stiffness parameter (K) can be tracked over time. For example, statistical techniques can be used to determine any changes over time (i.e., a stiffness change ($\Delta K$)). A statistical change in the stiffness parameter (K) can indicate that the FCF for the particular flow meter has changed.

The invention provides a stiffness parameter (K) that does not rely on stored or recalled calibration density values. This is in contrast to the prior art, where a known flow material is used in a factory calibration operation to obtain a density standard that can be used for all future calibration operations. The invention provides a stiffness parameter (K) that is obtained solely from vibrational responses of the flow meter. The invention provides a stiffness detection/calibration process without the need for a factory calibration process.

The interface 201 receives the vibrational response 210 from one of the velocity sensors 170L and 170R via the leads 100 of FIG. 1. The interface 201 can perform any necessary or desired signal conditioning, such as any manner of formatting, amplification, buffering, etc. Alternatively, some or all of the signal conditioning can be performed in the processing system 203. In addition, the interface 201 can enable communications between the meter electronics 20 and external devices. The interface 201 can be capable of any manner of electronic, optical, or wireless communication.

The interface 201 in one embodiment is coupled with a digitizer (not shown), wherein the sensor signal comprises an analog sensor signal. The digitizer samples and digitizes an analog vibrational response and produces the digital vibrational response 210.

The processing system 203 conducts operations of the meter electronics 20 and processes flow measurements from the flow meter assembly 10. The processing system 203 executes one or more processing routines and thereby processes the flow measurements in order to produce one or more flow characteristics.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204.

The storage system 204 can store flow meter parameters and data, software routines, constant values, and variable values. In one embodiment, the storage system 204 includes routines that are executed by the processing system 203, such as a stiffness routine 230 that determines the stiffness parameter (K) of the flow meter 5.

Figure 3:
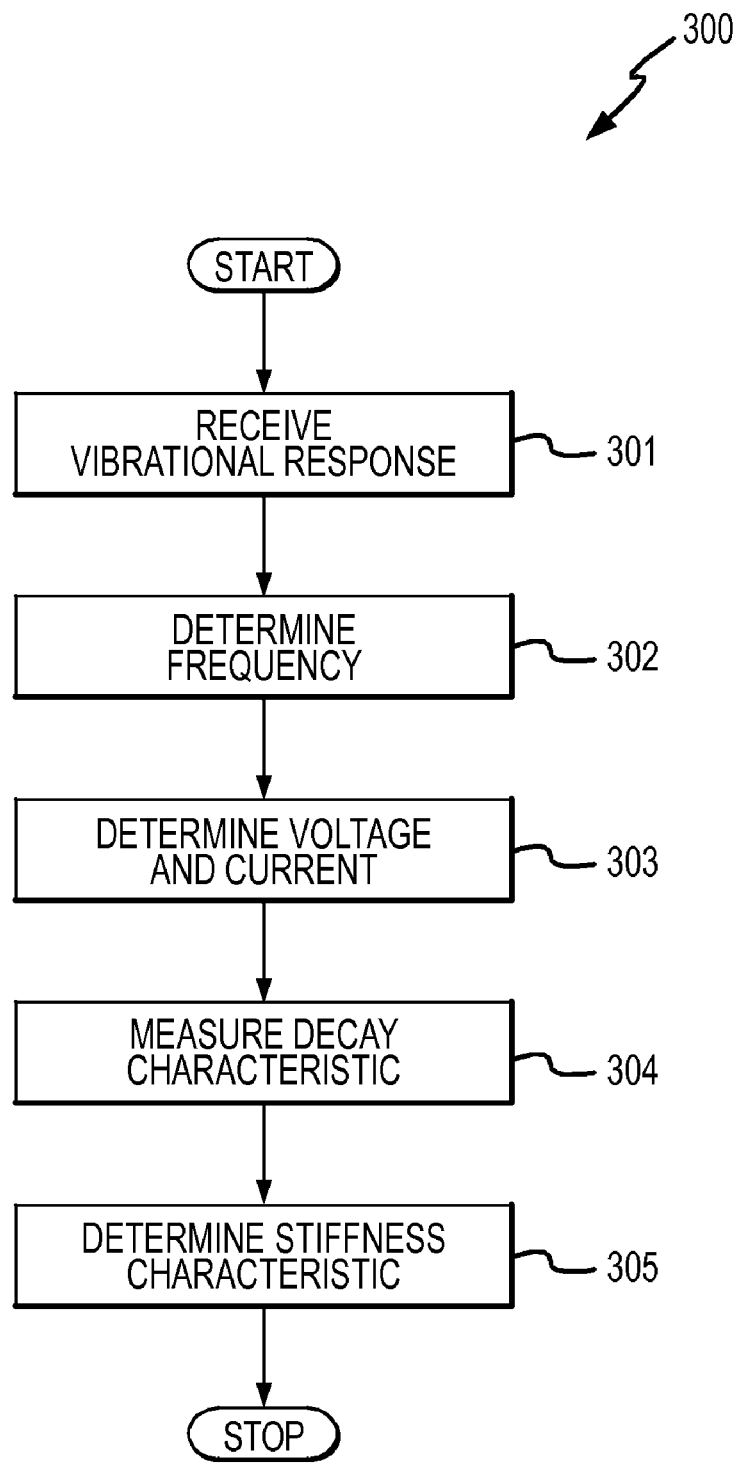
FIG. 3 is a flowchart of a method for determining a stiffness parameter (K) of a flow meter according to an embodiment of the invention.

The stiffness routine 230 in one embodiment can configure the processing system 203 to receive a vibrational response from the flow meter, with the vibrational response comprising a response to a vibration of the flow meter at a substantially resonant frequency, determine a frequency ($\omega_0$) of the vibrational response, determine a response voltage (V) and a drive current (I) of the vibrational response, measure a decay characteristic (ζ) of the flow meter, and determine the stiffness parameter (K) from the frequency ($\omega_0$), the response voltage (V), the drive current (I), and the decay characteristic (ζ) (see FIG. 3 and the accompanying discussion).

The stiffness routine 230 in one embodiment can configure the processing system 203 to receive the vibrational response, determine the frequency, determine the response voltage (V) and the drive current (I), measure the decay characteristic (ζ), and determine the stiffness parameter (K). The stiffness routine 230 in this embodiment further configures the processing system 203 to receive a second vibrational response from the flow meter at a second time $t_2$, repeat the determining and measuring steps for the second vibrational response in order to generate a second stiffness characteristic ($K_2$), compare the second stiffness characteristic ($K_2$) to the stiffness parameter (K), and detect the stiffness change (ΔK) if the second stiffness characteristic ($K_2$) differs from the stiffness parameter (K) by more than a tolerance 224 (see FIG. 4 and the accompanying discussion).

In one embodiment, the storage system 204 stores variables used to operate the flow meter 5. The storage system 204 in one embodiment stores variables such as the vibrational response 210, which can be received from the velocity/pick-off sensors 170L and 170R, for example.

In one embodiment, the storage system 204 stores constants, coefficients, and working variables. For example, the storage system 204 can store a determined stiffness characteristic 220 and a second stiffness characteristic 221 that is generated at a later point in time. The storage system 204 can store working values such as a frequency 212 of the vibrational response 210, a voltage 213 of the vibrational response 210, and a drive current 214 of the vibrational response 210. The storage system 204 can further store a vibrational target 226 and a measured decay characteristic 215 of the flow meter 5. In addition, the storage system 204 can store constants, thresholds, or ranges, such as the tolerance 224. Moreover, the storage system 204 can store data accumulated over a period of time, such as the stiffness change 228.

FIG. 3 is a flowchart 300 of a method for determining a stiffness parameter (K) of a flow meter according to an embodiment of the invention. In step 301, a vibrational response is received from the flow meter. The vibrational response is a response of the flow meter to a vibration at a substantially resonant frequency. The vibration can be continuous or intermittent. A flow material can be flowing through the meter assembly 10 or can be static.

In step 302, a frequency of the vibrational response is determined. The frequency $\omega_0$ can be determined from the vibrational response by any method, process, or hardware.

In step 303, the voltage (V or $V_{EMF}$) of the vibrational response is determined, along with the drive current (I). The voltage and drive current can be obtained from an unprocessed or a conditioned vibrational response.

In step 304, a damping characteristic of the flow meter is measured. The damping characteristic can be measured by allowing the vibrational response of the flow meter to decay down to a vibrational target while measuring the decay characteristic. This decaying action can be performed in several ways. The drive signal amplitude can be reduced, the driver 180 can actually perform braking of the meter assembly 10 (in appropriate flow meters), or the driver 180 can be merely unpowered until the target is reached. In one embodiment, the vibrational target comprises a reduced level in a drive setpoint. For example, if the drive setpoint is currently at 3.4 mV/Hz, then for the damping measurement the drive setpoint can be reduced to a lower value, such as 2.5 mV/Hz, for example. In this manner, the meter electronics 20 can let the meter assembly 10 simply coast until the vibrational response substantially matches this new drive target.

In step 305, the stiffness parameter (K) is determined from the frequency, the voltage, the drive current, and the decay characteristic (ζ). The stiffness parameter (K) can be determined according to equation (9), above. In addition to determining and tracking the stiffness (K), the method can also determine and track a damping parameter (C) and a mass parameter (M).

The method 300 can be iteratively, periodically, or randomly performed. The method 300 can be performed at predetermined landmarks, such as at a predetermined hours of operation, upon a change in flow material, etc.

Figure 4:
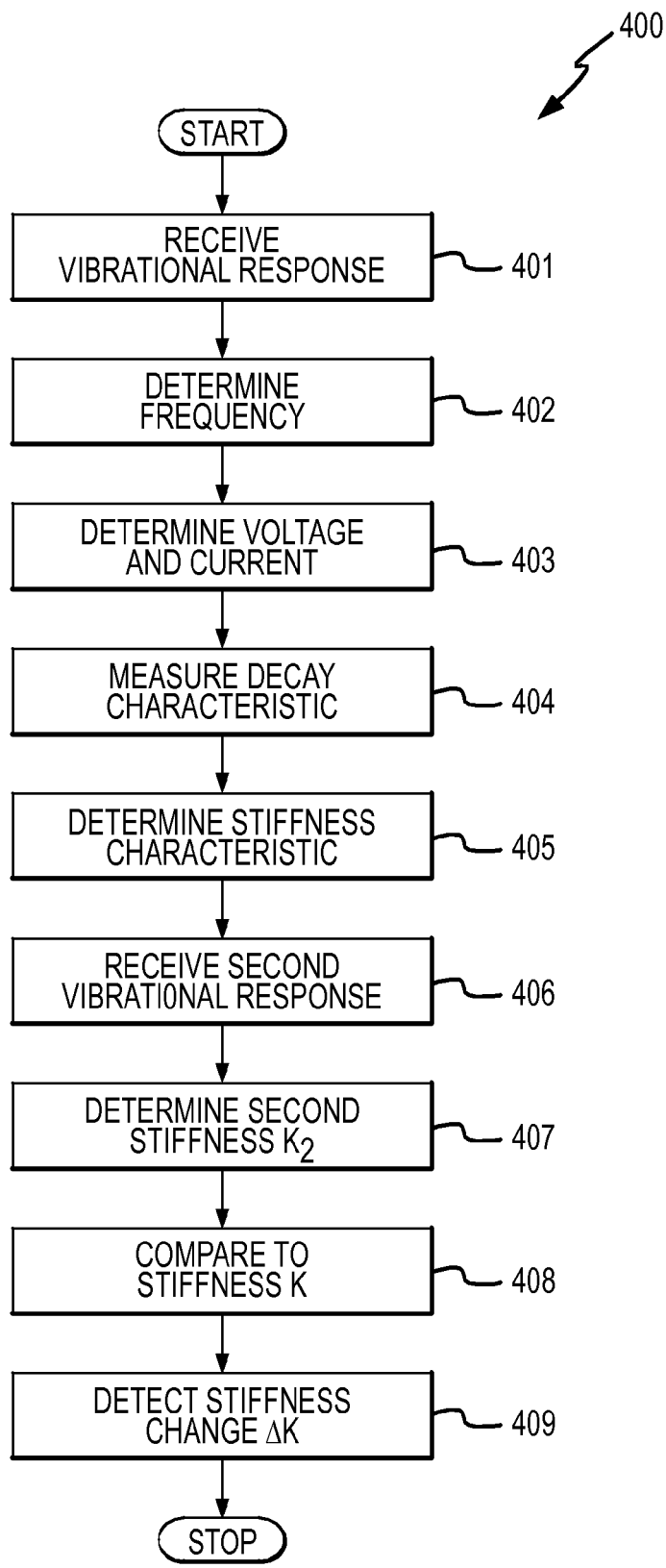
FIG. 4 is a flowchart of a method for determining a stiffness change ($\Delta K$) in a flow meter according to an embodiment of the invention.

FIG. 4 is a flowchart 400 of a method for determining a stiffness change (ΔK) in a flow meter according to an embodiment of the invention. In step 401, a vibrational response is received from the flow meter, as previously discussed.

In step 402, a frequency of the vibrational response is determined, as previously discussed.

In step 403, the voltage and drive current of the vibrational response are determined, as previously discussed.

In step 404, the decay characteristic (ζ) of the flow meter is measured, as previously discussed.

In step 405, the stiffness parameter (K) is determined from the frequency, the voltage, the drive current, and the decay characteristic (ζ), as previously discussed.

In step 406, a second vibrational response is received at a second time instance $t_2$. The second vibrational response is generated from a vibration of the meter assembly 10 at time $t_2$.

In step 407, a second stiffness characteristic $K_2$ is generated from the second vibrational response. The second stiffness characteristic $K_2$ can be generated using steps 401 through 405, for example.

In step 408, the second stiffness characteristic $K_2$ is compared to the stiffness parameter (K). The comparison comprises a comparison of stiffness characteristics that are obtained at different times in order to detect a stiffness change (ΔK).

In step 409, any stiffness change (ΔK) between $K_2$ and K is determined. The stiffness change determination can employ any manner of statistical or mathematical method for determining a significant change in stiffness. The stiffness change (ΔK) can be stored for future use and/or can be transmitted to a remote location. In addition, the stiffness change (ΔK) can trigger an alarm condition in the meter electronics 20. The stiffness change (ΔK) in one embodiment is first compared to the tolerance 224. If the stiffness change (ΔK) exceeds the tolerance 224, then an error condition is determined. In addition to determining and tracking the stiffness (K), the method can also determine and track a damping parameter (C) and a mass parameter (M).

The method 400 can be iteratively, periodically, or randomly performed. The method 400 can be performed at predetermined landmarks, such as at a predetermined hours of operation, upon a change in flow material, etc.

Figure 5:
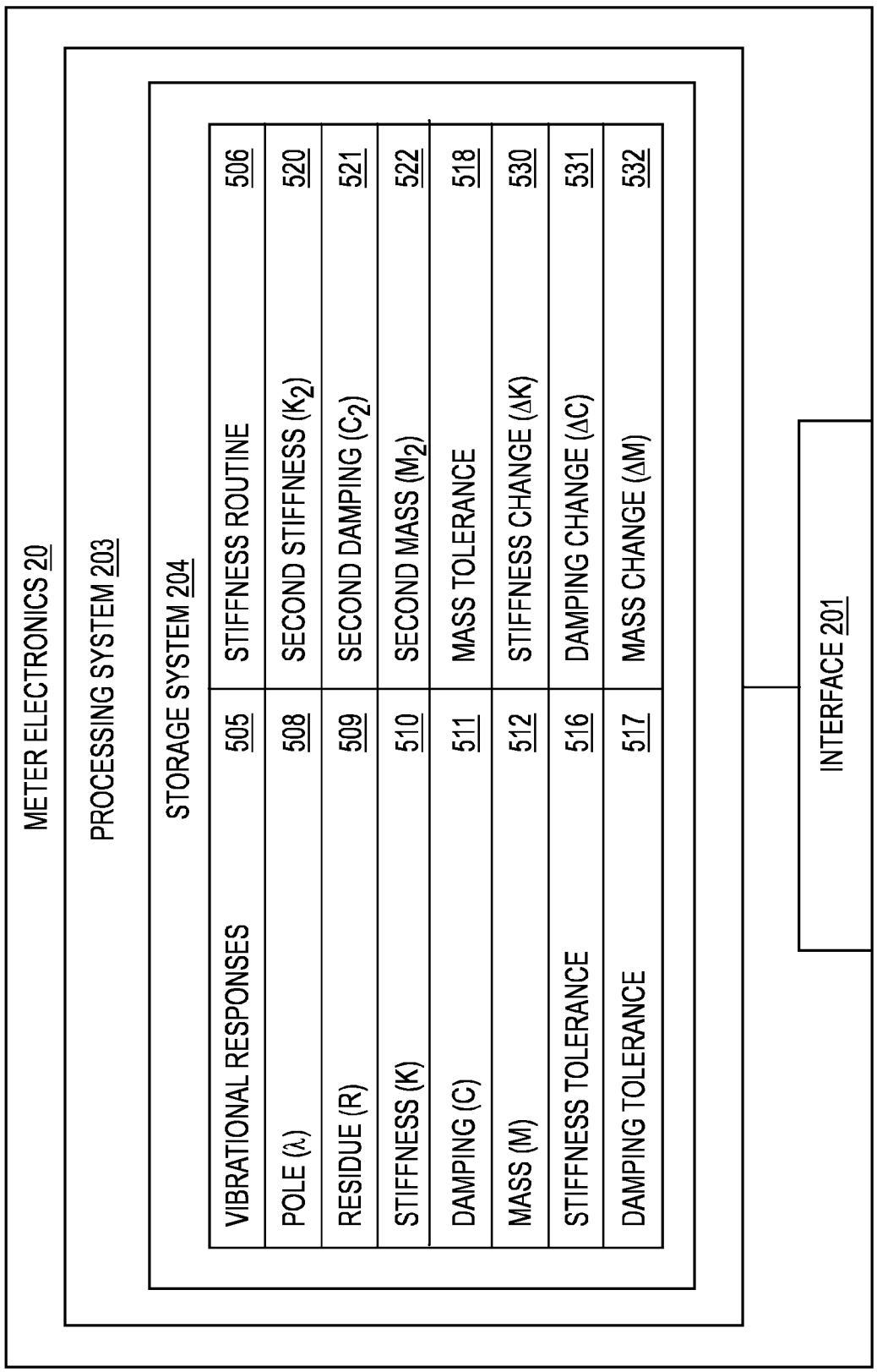
FIG. 5 shows the meter electronics according to another embodiment of the invention.

FIG. 5 shows the meter electronics 20 according to another embodiment of the invention. The meter electronics 20 in this embodiment can include the interface 201, the processing system 203, and the storage system 204, as previously discussed. The meter electronics 20 receives three or more vibrational responses 505, such as from the meter assembly 10, for example. The meter electronics 20 processes the three or more vibrational responses 505 in order to obtain flow characteristics of the flow material flowing through the meter assembly 10. In addition, the three or more vibrational responses 505 are also processed in order to determine a stiffness parameter (K) of the meter assembly 10. The meter electronics 20 can further determine a damping parameter (C) and a mass parameter (M) from the three or more vibrational responses 505. These meter assembly parameters can be used to detect changes in the meter assembly 10, as previously discussed.

The storage system 204 can store processing routines, such as the stiffness routine 506. The storage system 204 can store received data, such as the vibrational responses 505. The storage system 204 can store pre-programmed or user-entered values, such as the stiffness tolerance 516, the damping tolerance 517, and the mass tolerance 518. The storage system 204 can store working values, such as the pole ($\lambda$) 508 and the residue (R) 509. The storage system 204 can store determined final values, such as the stiffness (K) 510, the damping (C) 511, and the mass (M) 512. The storage system 204 can store comparison values generated and operated on over periods of time, such as a second stiffness ($K_2$) 520, a second damping ($C_2$) 521, a second mass ($M_2$) 522, a stiffness change ($\Delta K$) 530, a damping change ($\Delta C$) 531, and a mass change ($\Delta M$) 532. The stiffness change ($\Delta K$) 530 can comprise a change in the stiffness parameter (K) of the meter assembly 10 as measured over time. The stiffness change ($\Delta K$) 530 can be used to detect and determine physical changes to the meter assembly 10 over time, such as corrosion and erosion effects. In addition, the mass parameter (M) 512 of the meter assembly 10 can be measured and tracked over time and stored in a mass change ($\Delta M$) 532 and a damping parameter (C) 511 can be measured over time and stored in a damping change ($\Delta C$) 531. The mass change ($\Delta M$) 532 can indicate the presence of build-up of flow materials in the meter assembly 10 and the damping change ($\Delta C$) 531 can indicate changes in a flow tube, including material degradation, erosion and corrosion, cracking, etc.

In operation, the meter electronics 20 receives three or more vibrational responses 505 and processes the vibrational responses 505 using the stiffness routine 506. In one embodiment, the three or more vibrational responses 505 comprise five vibrational responses 505, as will be discussed below. The meter electronics 20 determines the pole ($\lambda$) 508 and the residue (R) 509 from the vibrational responses 505. The pole ($\lambda$) 508 and residue (R) 509 can comprise a first order pole and residue or can comprise a second order pole and residue. The meter electronics 20 determines the stiffness parameter (K) 510, the damping parameter (C) 511, and the mass parameter (M) 512 from the pole ($\lambda$) 508 and the residue (R) 509. The meter electronics 20 can further determine a second stiffness ($K_2$) 520, can determine a stiffness change ($\Delta K$) 530 from the stiffness parameter (K) 510 and the second stiffness ($K_2$) 520, and can compare the stiffness change ($\Delta K$) 530 to a stiffness tolerance 516. If the stiffness change ($\Delta K$) 530 exceeds the stiffness tolerance 516, the meter electronics 20 can initiate any manner of error recordation and/or error processing routine. Likewise, the meter electronics 20 can further track the damping and mass parameters over time and can determine and record a second damping ($C_2$) 521 and a second mass ($M_2$), and a resulting damping change ($\Delta C$) 531 and mass change ($\Delta M$) 532. The damping change ($\Delta C$) 531 and the mass change ($\Delta M$) 532 can likewise be compared to a damping tolerance 517 and a mass tolerance 518.

The invention can be illustrated with a mathematical model. The vibrational response of a flow meter can be represented by an open loop, second order drive model, comprising:

$$M\ddot{x}+C\dot{x}+Kx=f(t) \qquad (10)$$

where f is the force applied to the system, M is a mass parameter of the system, C is a damping parameter, and K is a stiffness parameter. The term K comprises $K=M(\omega_0)2$ and the term C comprises $C=M2\zeta\omega_0$, where $\omega_0=2\pi f_0$ and $f_0$ is the resonant frequency of the meter assembly 10 in Hertz. The term comprises a decay characteristic measurement obtained from the vibrational response, as previously discussed. In addition, x is the physical displacement distance of the vibration, $\dot{x}$ is the velocity of the flowtube displacement, and $\ddot{x}$ is the acceleration. This is commonly referred to as the MCK model. This formula can be rearranged into the form:

$$(ms^2+cs+k)X(s)=F(s)+(ms+c)x(0)+m\dot{x}(0) \qquad (11)$$

Equation (11) can be further manipulated into a transfer function form, while ignoring the initial conditions. The result is:

$$H(s) = \frac{\text{output}}{\text{input}} = \frac{X(s)}{F(s)} = \frac{\frac{1}{m}}{s^2 + \frac{cs}{m} + \frac{k}{m}} \qquad (12)$$

Further manipulation can transform equation (12) into a first order pole-residue frequency response function form, comprising:

$$H(\omega) = \frac{R}{(j\omega - \lambda)} + \frac{\overline{R}}{(j\omega - \overline{\lambda})} \qquad (13)$$

where $\lambda$ is the pole, R is the residue, the term (j) comprises the square root of $-1$, and $\omega$ is the circular excitation frequency (in radians per second).

The system parameters comprising the natural/resonant frequency ($\omega_n$), the damped natural frequency ($\omega_d$), and the decay characteristic ($\zeta$) are defined by the pole.

$$\omega_n = |\lambda| \qquad (14)$$

$$\omega_d = \text{imag}(\lambda) \qquad (15)$$

$$\zeta = \frac{\text{real}(\lambda)}{\omega_n} \qquad (16)$$

The stiffness parameter (K), the damping parameter (C), and the mass parameter (M) of the system can be derived from the pole and residue.

$$M = \frac{1}{2jR\omega_d} \qquad (17)$$

$$K = \omega_n^2 M \qquad (18)$$

$$C = 2\zeta\omega_n M \qquad (19)$$

Consequently, the stiffness parameter (K), the mass parameter (M), and the damping parameter (C) can be calculated based on a good estimate of the pole ($\lambda$) and the residue (R).

The pole and residue are estimated from the measured frequency response functions. The pole ($\lambda$) and the residue (R) can be estimated using some manner of direct or iterative computational method.

The response near the drive frequency is composed of primarily the first term of equation (13), with the complex conjugate term contributing only a small, nearly constant "residual" part of the response. As a result, equation (13) can be simplified to:

$$H(\omega) = \frac{R}{(j\omega - \lambda)} \quad (20)$$

In equation (20), the H(ω) term is the measured frequency response function (FRF), obtained from the three or more vibrational responses. In this derivation, H is composed of a displacement output divided by a force input. However, with the voice coil pickoffs typical of a Coriolis flow meter, the measured FRF (i.e., a Ḣ term) is in terms of velocity divided by force. Therefore, equation (20) can be transformed into the form:

$$\dot{H}(\omega) = H(\omega) \cdot j\omega = \frac{j\omega R}{(j\omega - \lambda)} \quad (21)$$

Equation (21) can be further rearranged into a form that is easily solvable for the pole (λ) and the residue (R).

$$\dot{H} j\omega - \dot{H}\lambda = j\omega R \quad (22)$$

$$\dot{H} = R + \frac{\dot{H}}{j\omega}\lambda$$

$$\begin{bmatrix} 1 & \frac{\dot{H}}{j\omega} \end{bmatrix} \begin{Bmatrix} R \\ \lambda \end{Bmatrix} = \dot{H}$$

Equation (22) forms an over-determined system of equations. Equation (22) can be computationally solved in order to determine the pole (λ) and the residue (R) from the velocity/force FRF (Ḣ). The terms H, R, and λ are complex.

In one embodiment, the forcing frequency ω is 5 tones. The 5 tones in this embodiment comprise the drive frequency and 2 tones above the drive frequency and 2 tones below. The tones can be separated from the fundamental frequency by as little as 0.5-2 Hz. However, the forcing frequency ω can comprise more tones or fewer tones, such as a drive frequency and 1 tone above and below. However, 5 tones strikes a good compromise between accuracy of the result and the processing time needed to obtain the result.

Note that in the preferred FRF measurement, two FRFs are measured for a particular drive frequency and vibrational response. One FRF measurement is obtained from the driver to the right pickoff (RPO) and one FRF measurement is obtained from the driver to the left pickoff (LPO). This approach is called single input, multiple output (SIMO). In a distinguishing new feature of this invention, a SIMO technique is used to better estimate the pole (λ) and the residue (R). Previously, the two FRFs were used separately to give two separate pole (λ) and residue (R) estimates. Recognizing that the two FRFs share a common pole (λ) but separate residues ($R_L$) and ($R_R$), the two measurements can be combined advantageously to result in a more robust pole and residue determination.

$$\begin{bmatrix} 1 & 0 & \frac{\dot{H}_{LPO}}{j\omega} \\ 0 & 1 & \frac{\dot{H}_{RPO}}{j\omega} \end{bmatrix} \begin{Bmatrix} R_L \\ R_R \\ \lambda \end{Bmatrix} = \dot{H} \quad (23)$$

Equation (23) can be solved in any number of ways. In one embodiment, the equation is solved through a recursive least squares approach. In another embodiment, the equation is solved through a pseudo-inverse technique. In yet another embodiment, because all of the measurements are available simultaneously, a standard Q-R decomposition technique can be used. The Q-R decomposition technique is discussed in Modern Control Theory, William Brogan, copyright 1991, Prentice Hall, pp. 222-224, 168-172.

In use, the stiffness parameter (K), along with the damping parameter (C) and the mass parameter (M), can be tracked over time. For example, statistical techniques can be used to determine any changes in the stiffness parameter (K) over time (i.e., a stiffness change (ΔK)). A statistical change in the stiffness parameter (K) can indicate that the FCF for the particular flow meter has changed.

The invention provides a stiffness parameter (K) that does not rely on stored or recalled calibration density values. This is in contrast to the prior art, where a known flow material is used in a factory calibration operation to obtain a density standard that can be used for all future calibration operations. The invention provides a stiffness parameter (K) that is obtained solely from vibrational responses of the flow meter. The invention provides a stiffness detection/calibration process without the need for a factory calibration process.

Figure 6:
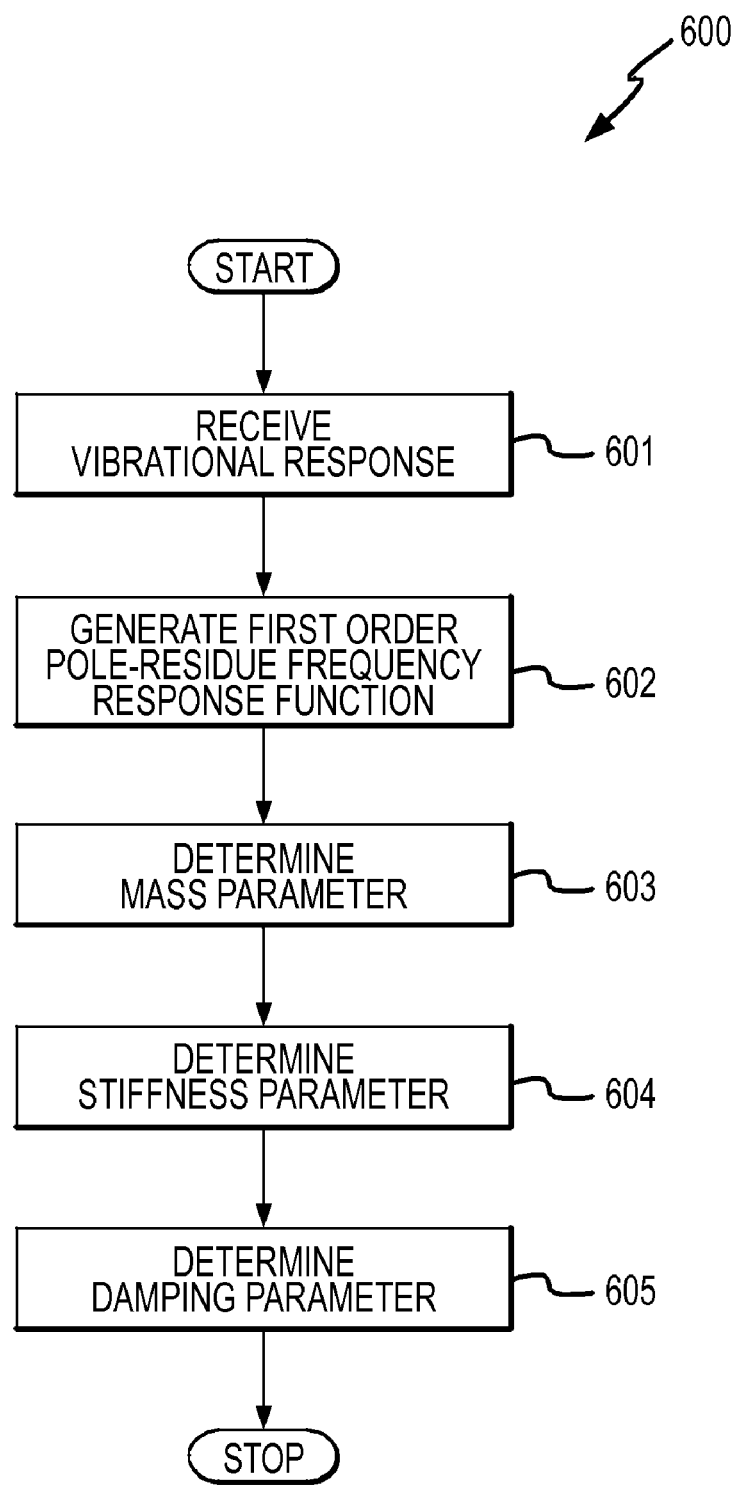
FIG. 6 is a flowchart of a method for determining a stiffness parameter (K) of a flow meter according to an embodiment of the invention.

FIG. 6 is a flowchart 600 of a method for determining a stiffness parameter (K) of a flow meter according to an embodiment of the invention. In step 601, three or more vibrational responses are received. The three or more vibrational responses can be received from the flow meter. The three or more vibrational responses can include a substantially fundamental frequency response and two or more non-fundamental frequency responses. In one embodiment, one tone above the fundamental frequency response is received and one tone below the fundamental frequency response is received. In another embodiment, two or more tones above the fundamental frequency response are received and two or more tones below the fundamental frequency response are received.

In one embodiment, the tones are substantially equidistantly spaced above and below the fundamental frequency response. Alternatively, the tones are not equidistantly spaced.

In step 602, a first order pole-residue frequency response is generated from the three or more vibrational responses. The first order pole-residue frequency response takes the form given in equation (23).

In step 603, the mass parameter (M) is determined from the first order pole-residue frequency response. The mass parameter (M) is determined by determining the first order pole (λ) and the first order residue (R) of the vibrational responses. Then, the natural frequency $\omega_n$, the damped natural frequency $\omega_d$, and the decay characteristic (ζ) are determined from the first order pole (λ) and residue (R). Subsequently, the damped natural frequency $\omega_d$, the residue (R), and the imaginary term (j) are plugged into equation (17) in order to obtain the mass parameter (M).

In step 604, the stiffness parameter (K) is determined from the solution of equation (18). The solution employs the natural frequency $\omega_n$ and the determined mass parameter (M) from step 603 are plugged into equation (18) in order to obtain the stiffness parameter (K).

In step 605, the damping parameter (C) is determined from the solution of equation (19). The solution employs the decay characteristic ($\zeta$), the natural frequency $\omega_n$, and the determined mass parameter (M).

Figure 7:
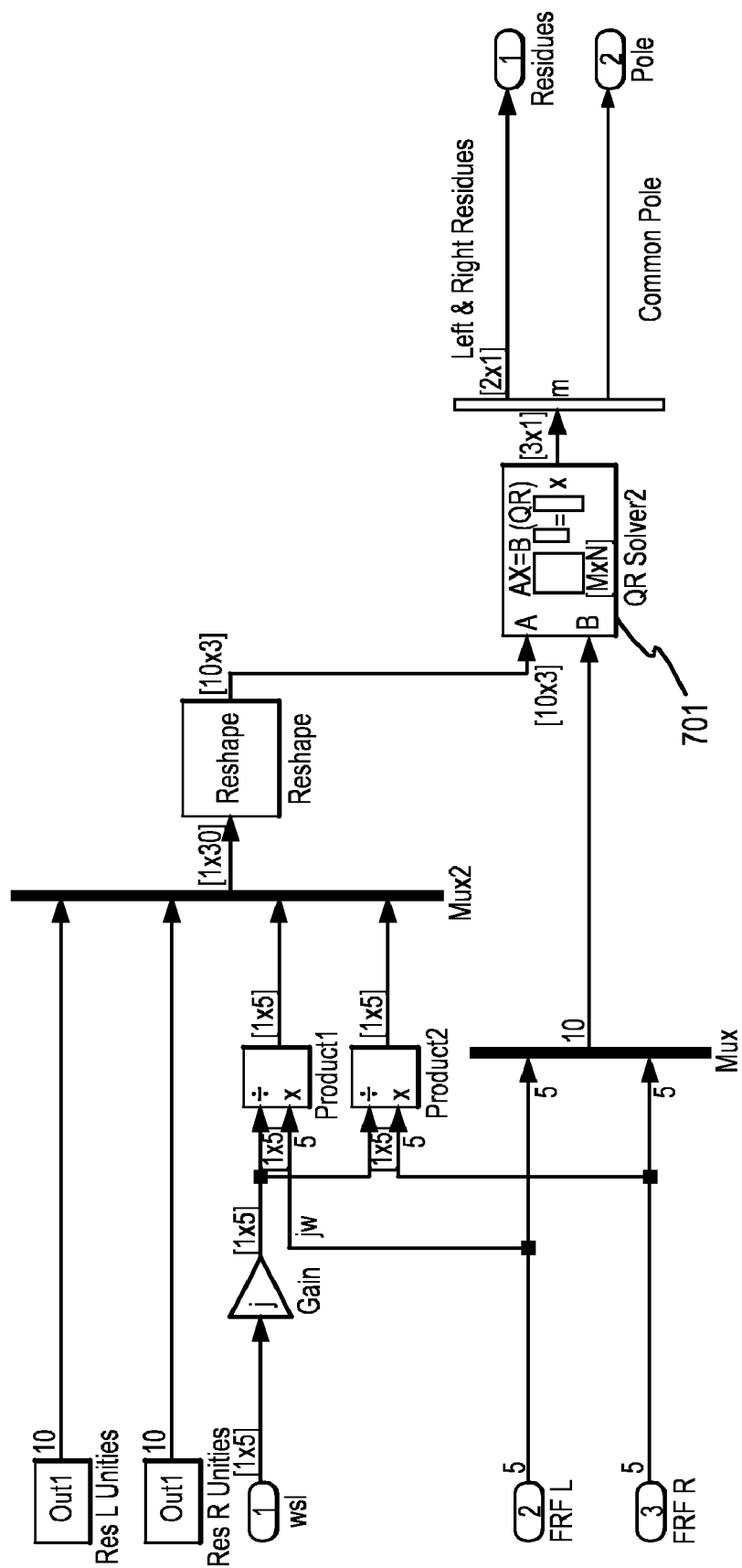
FIG. 7 shows an implementation of the pole ($\lambda$) and residue (R) solutions according to an embodiment of the invention.

FIG. 7 shows an implementation of the pole ($\lambda$) and residue (R) solutions according to an embodiment of the invention. The implementation follows equation (23). The FRF inputs are at the left of the diagram. These FRF inputs are the five frequencies at which FRF coefficients are calculated in this embodiment (four test signal frequencies and the drive frequency). The FRF_L and FRF_R inputs are the driver-pickoff complex FRF coefficients calculated at those frequencies, corresponding to $H_{LPO}$ and $H_{RPO}$ in equation (23). The FRF coefficients are passed into the B input of the QR solver block 701. The A matrix for the QR solver block 701 is formed from the FRF coefficients divided by $j\omega$ on a term-by-term basis and comprises columns of 1's and 0's to conform with equation (23). The matrix is reshaped into the proper [10×3] complex dimensions and passed into the A input of the QR solver block 701. The x vector output of the QR solver block 701 comprises the left and right residues $R_L$ and $R_R$ and the pole $\lambda$. These outputs are passed out of the QR block 701 for processing in order to generate the system parameters.

Figure 8:
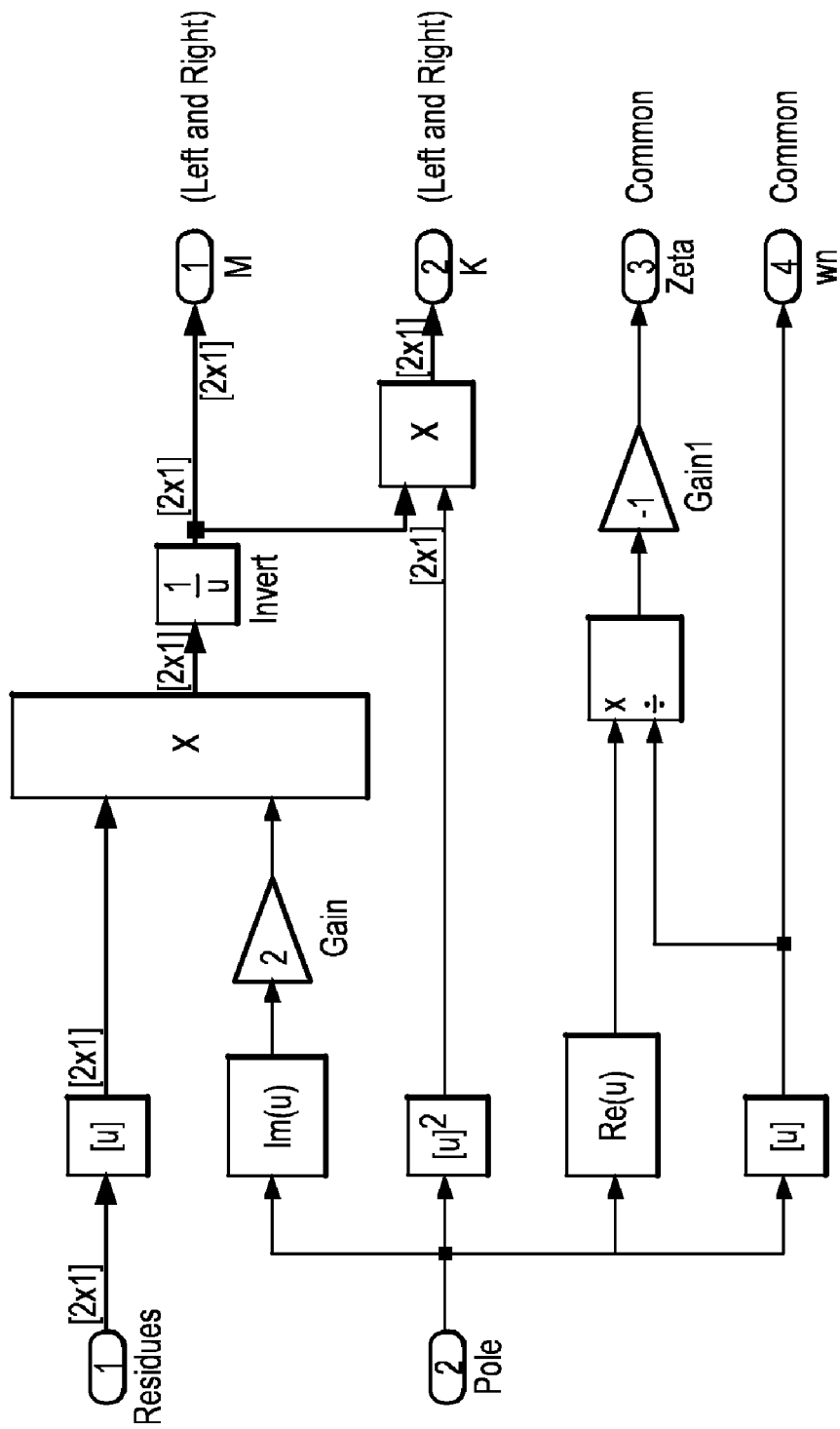
FIG. 8 is a block diagram showing the calculation of the M, C, and K system parameters according to an embodiment of the invention.

FIG. 8 is a block diagram showing the calculation of the M, C, and K system parameters according to an embodiment of the invention. The implementation determines the M, C, and K system parameters from the pole and residue estimates per equations (14-16) and equations (17-19). The residues are purely imaginary for a real normal modal model. However, there will always be some real part due to noise in the measurement data and due to model-fitting numerical precision issues. Therefore, the absolute value of the residue is used, which has a similar effect as dividing by j per equation (17). The mass and stiffness are calculated using the pole and residue per equations (17-18). Note that there is a "Left" and "Right" mass and stiffness, i.e., the mass and stiffness calculated from the FRFs of the LPO/Driver and the RPO/Driver. The mass and stiffness estimates may differ from right to left due to asymmetries in the coils and magnets and in the structure itself. Changes in the differences or the difference ratios indicate a non-uniform change in mass or stiffness and can be exploited to give additional diagnostic information about changes to the FCF or the integrity of the flow meter.

Two other outputs from the system parameter calculations are the damping coefficient, zeta or $\zeta$, and the natural frequency $\omega_n$. This embodiment gives a more over-determined or better estimated set of global parameters.

The estimate of $\omega_n$ makes a good quality check for the closed loop drive system. If the drive is indeed operating at resonance, the drive frequency should agree to within a few milliHertz to the natural frequency estimate. If the difference in more than a few milliHertz, a warning flag can be set, indicating that the drive system is not operating properly or that the current stiffness estimate is suspect.

Figure 9:
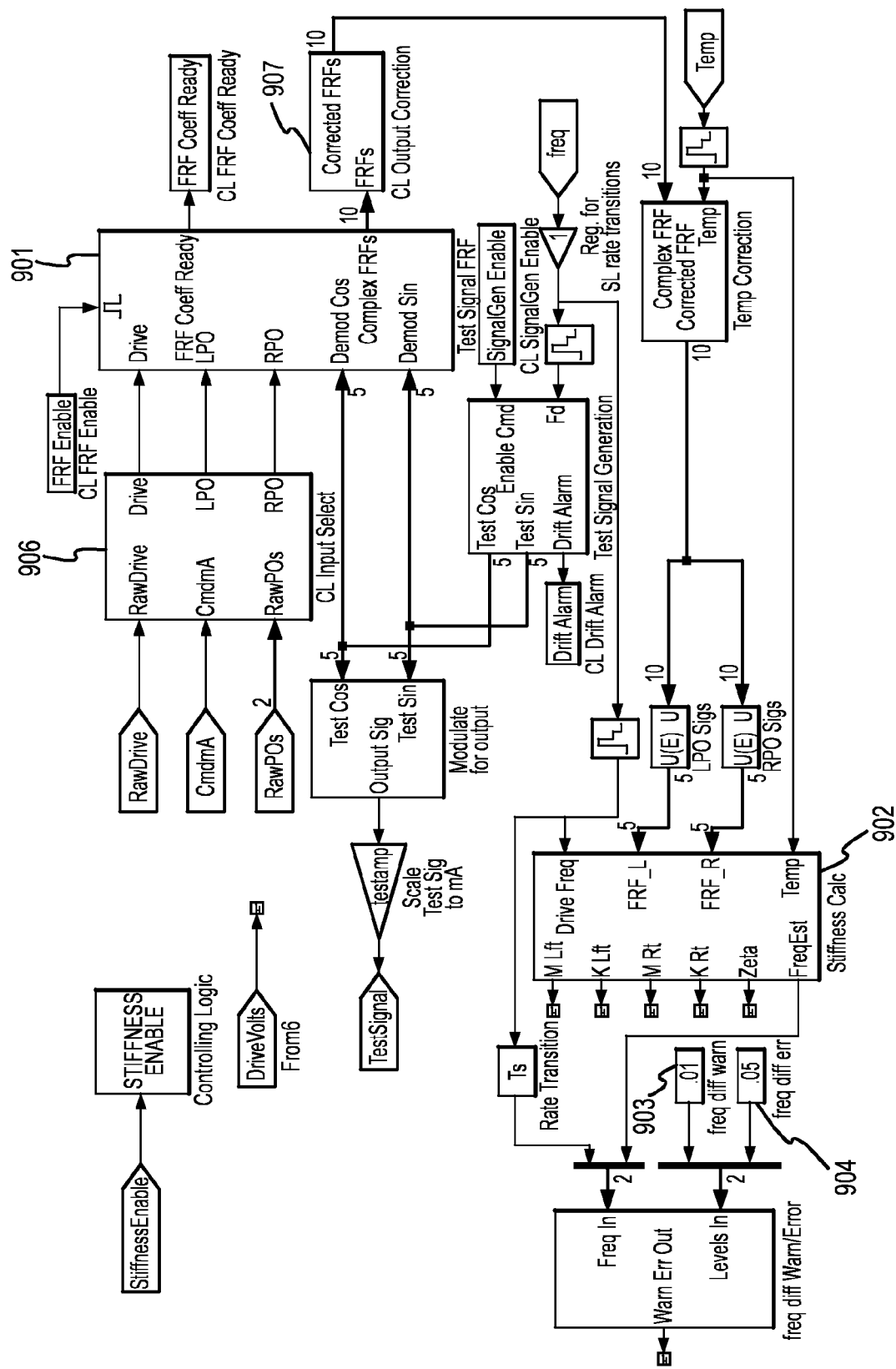
FIG. 9 shows an overall FRF-based stiffness estimation system according to an embodiment of the invention.

FIG. 9 shows an overall FRF-based stiffness estimation system according to an embodiment of the invention. There are seven distinct inputs to the stiffness estimation subsystem, indicated by pentagons that are signal sources (five on the top left, and two on the far right). The "RawDrive" and "Raw-POs" inputs are the raw readings of the pickoff voltages and the drive current. These signals are down-sampled to 2 kHz by decimation, for example, and are then fed into the FRF coefficient estimation subsystem. The "CmdmA" input is the commanded current that is taken from the output of a corresponding digital drive system. The "StiffnessEnable" estimate is a logical input, allowing the digital drive system to control when the FCF validation algorithm is active. The "freq" input is the drive frequency, as estimated by the digital drive system. It is input to the test signal generator subsystem and the stiffness calculation subsystem.

The FRF Stiffness calculation block 902 outputs the system parameter estimates M & K Lft and Rt as well as Zeta and FreqEst. These are the primary diagnostic outputs used in FCF validation. The figure also shows a freq diff Warn block 903 and a freq diff Error block 904 that implement the drive quality check discussed above by comparing the drive frequency to the estimated natural frequency.

Measuring the FRF would normally require a current measurement, necessitating an additional analog-to-digital (A/D) converter. However, this embodiment uses a calibrated commanded current, obviating the need for an additional A/D converter. The CL Input Select block 906 and the CL Output Correction block 907 implement the calibration algorithm. The calibration process uses the "Test Signal FRF" block 901 to calculate the frequency response function of the actual (RawDrive) current to the commanded current (CmdmA) at one state of the controlling logic. During the FCF validation logic state, the FRF between the raw POs and the commanded current is calculated and corrected by the raw to commanded current FRF coefficients to give the FRFs used for further processing.

The FRF stiffness estimation algorithm outputs the "TestSignal" output at the center left of the diagram of the figure. This test signal output contains excitation at the four test frequencies that are added to the drive command immediately before output. These test signals are added to the digital drive signal when FCF validation is enabled.

The logic is such that when the FCF validation is off, the digital drive signal passes right through a switch or other device, where it is upsampled from its base rate (typically 4 kHz) by the interpolation filter to the appropriate output rate, typically 8 kHz. When FCF validation is enabled, the test signals, upsampled from 2 to 4 kHz, are added to the digital drive signal. The drive signal then consists of the closed loop drive frequency signal and the 4 test tones, all of which then go through the upsample filter.

The FCF validation procedure is desirably transparent to the drive system. In one embodiment, the test signals are removed from the pickoffs to ensure a good frequency and amplitude estimate for the closed loop drive. This is done with a set of notch filters tuned to the exact frequencies of the test signals.

In another embodiment, the pole-residue approach can employ a second-order pole-residue frequency response function in order to achieve a better result. A second order pole-residue approach provides a truer fit to the real data than a first order pole-residue 10 approach. The trade-off is a greater numerical complexity and increased processing time.

The MCK embodiment of the stiffness estimation begins with a simple second order system model, as shown in equation (24), below. Since the pickoffs on the flow meter measure velocity, not position, the equation is differentiated and then evaluated at a particular frequency $\omega$.

$$H(s) = \frac{X(s)}{F(s)} = \frac{1}{Ms^2 + Cs + K} \qquad (24)$$

$$\dot{H}(s) = \frac{\dot{X}(s)}{F(s)} = \frac{s}{Ms^2 + Cs + K}$$

$$\dot{H}(\omega) = \frac{\dot{X}(\omega)}{F(\omega)} = \frac{j\omega}{-M\omega^2 + jC\omega + K}$$

Since the goal is to solve for M, C, and K from measurements of drive current (or force) and pickoff voltage (or velocity), it is convenient to rewrite equation (24) to isolate the unknowns. This produces equation (25).

$$K - M\omega^2 + jC\omega = \frac{j\omega}{\dot{H}(\omega)} \quad (25)$$

At this point the equation may be separated into real and imaginary parts.

$$K - M\omega^2 = \text{Re}\left\{\frac{j\omega}{\dot{H}(\omega)}\right\} \quad (26)$$

$$C\omega = \text{Im}\left\{\frac{j\omega}{\dot{H}(\omega)}\right\}$$

Expanding out $$\frac{j\omega}{\dot{H}(\omega)},$$

equation (26) can be rewritten as:

$$K - M\omega^2 = \frac{\omega\text{Im}\{\dot{H}(\omega)\}}{|\dot{H}(\omega)|^2} \quad (27)$$

$$C\omega = \frac{\omega\text{Re}\{\dot{H}(\omega)\}}{|\dot{H}(\omega)|^2}$$

The second equation is now a simple, algebraic solution. In order to further simplify the first part of the equation, the measured resonant drive frequency is employed. Since $\omega_n = \sqrt{K/M}$, it may be found that:

$$K - \frac{K}{\omega_n^2} = \frac{\omega\text{Im}\{\dot{H}(\omega)\}}{|\dot{H}(\omega)|^2} \quad (28)$$

$$K\left(\frac{\omega_n^2 - \omega^2}{\omega_n^2}\right) = \frac{\omega\text{Im}\{\dot{H}(\omega)\}}{|\dot{H}(\omega)|^2}$$

$$K = \frac{\omega_n^2 \omega \text{Im}\{\dot{H}(\omega)\}}{(\omega_n^2 - \omega^2)|\dot{H}(\omega)|^2}$$

so long as $\omega \neq \omega_n$. Backing out M from this solution for K, the three solutions for M, C, and K are given in equation (29).

$$K = \frac{\omega_n^2 \omega \text{Im}\{\dot{H}(\omega)\}}{(\omega_n^2 - \omega^2)|\dot{H}(\omega)|^2} \quad (29)$$

$$M = \frac{K}{\omega_n^2}$$

$$C = \frac{\text{Re}\{\dot{H}(\omega)\}}{|\dot{H}(\omega)|^2}$$

Note that given the resonant frequency $\omega_n$, a driver-pickoff FRF at one particular frequency $\omega_l$ is sufficient to solve the equations and determine the parameters M, C, and K. This is particularly useful; when FRFs are taken at multiple frequencies the least-squares fit to the data is simply the average of the individual estimates of each coefficient. This is a good deal simpler than the pseudo inverse that typically would have to be performed. Note, though, that the restriction that $\omega \neq \omega_n$ precludes the use of the resonant drive FRF in the solution for K or M. This is not particularly surprising since the height of a peak at a resonance is determined solely by the damping. One potential shortcoming of this approach, though, is that the parameters estimated from left and right pickoff data are necessarily independent of each other. This is in contrast to the pole-residue method, where some benefit is gained by restricting the left and right pickoffs to estimate the same pole, despite their differences in amplitude.

Figure 10:
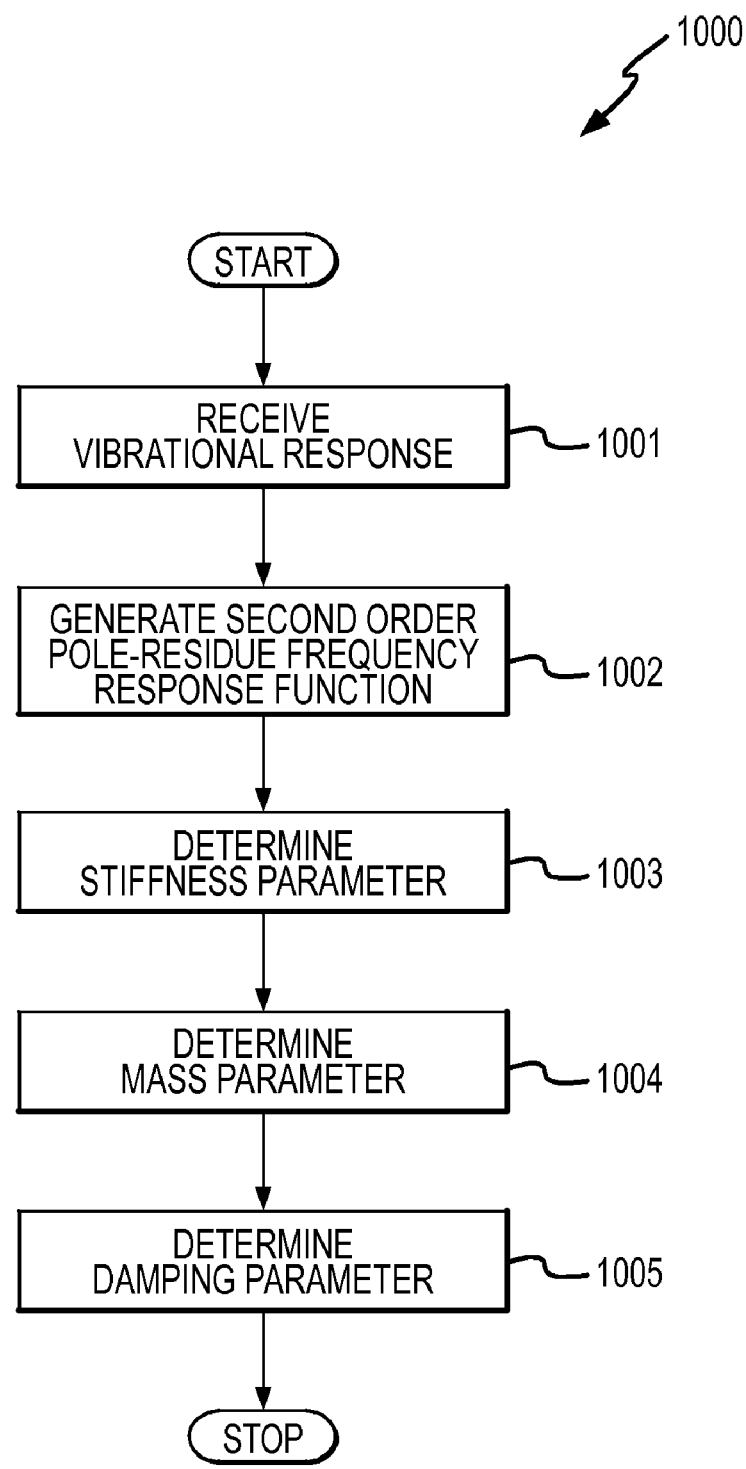
FIG. 10 is a flowchart of a method for determining a stiffness parameter (K) of a flow meter according to an embodiment of the invention.

FIG. 10 is a flowchart 1000 of a method for determining a stiffness parameter (K) of a flow meter according to an embodiment of the invention. In step 1001, three or more vibrational responses are received, as previously discussed.

In step 1002, a second order pole-residue frequency response is generated from the three or more vibrational responses. The second order pole-residue frequency response takes the form given in equation (24).

In step 1003, the stiffness parameter (K) is determined from the solution of equation (29). The solution employs the natural frequency $\omega_n$, the one or more frequency tones $\omega$, the imaginary portion of the FRF (i.e., an imaginary component of $\dot{H}(\omega)$), and an amplitude of the FRF (i.e., the absolute value of $\dot{H}(\omega)$).

In step 1004, the mass parameter (M) is determined from the second order pole-residue frequency response. The mass parameter (M) is determined from the solution of equation (29) and is obtained using the stiffness parameter (K) and the natural frequency $\omega_n$.

In step 1005, the damping parameter (C) is determined from the second order pole-residue frequency response. The damping parameter (C) is determined from the solution of equation (29) and is obtained using the one or more frequency tones $\omega$, the real portion of the FRF (i.e., a real component of $\dot{H}(\omega)$), and an amplitude of the FRF (i.e., the absolute value of $\dot{H}(\omega)$).

Figure 11:
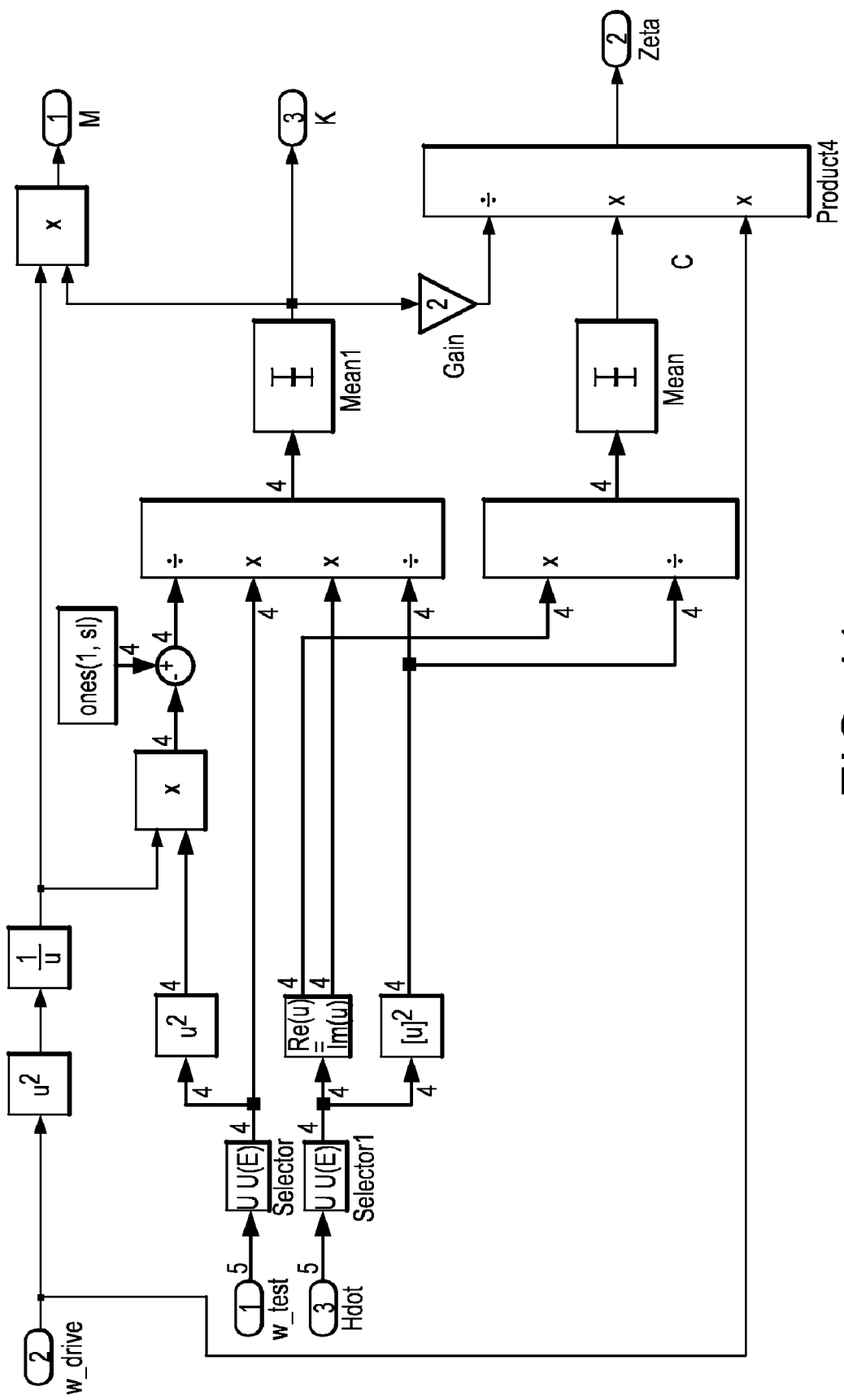
FIG. 11 shows the implementation of the M, C, and K solutions for the second order pole-residue response from equations (29) according to an embodiment of the invention.

FIG. 11 shows the implementation of the M, C, and K solutions for the second order pole-residue response from equations (29) according to an embodiment of the invention. The inputs appear as oval input ports at the left of the diagram. These are the measured drive frequency $\omega\_drive$, which is used in equations (29) as $\omega_n$, the five frequencies at which FRF coefficients have been calculated (four test signal frequencies and the drive frequency, represented by $\omega\_test$), and the driver-pickoff complex FRF coefficients calculated at those frequencies ($\dot{H}$ or Hdot). The drive frequency FRF is discarded by the selector blocks, since it cannot be used in the M and K solutions as described earlier. The K solution is computed as $$K = \frac{\omega\text{Im}\{\dot{H}(\omega)\}}{\left(1 - \frac{\omega^2}{\omega_n^2}\right)|\dot{H}(\omega)|^2} \quad (30)$$

which is an equivalent form of the solution given in equations (29). The solution for C is the same form as the derived solution in equations (29), and M is directly computed from the solution for K. Note the averaging operation that is applied to each coefficient estimate. This averaging results in solutions that are least-squares fits to the input data. Finally, given the M, C, and K estimates, the decay characteristic (ζ or zeta) is computed as:

$$\zeta = \frac{C\omega_n}{2K} \qquad (31)$$

The decay characteristic (ζ) is considered a more useful parameter than the damping parameter C. Therefore, the mass M, stiffness K, and decay characteristic (ζ) are the outputs of the measurement.

Figure 12:
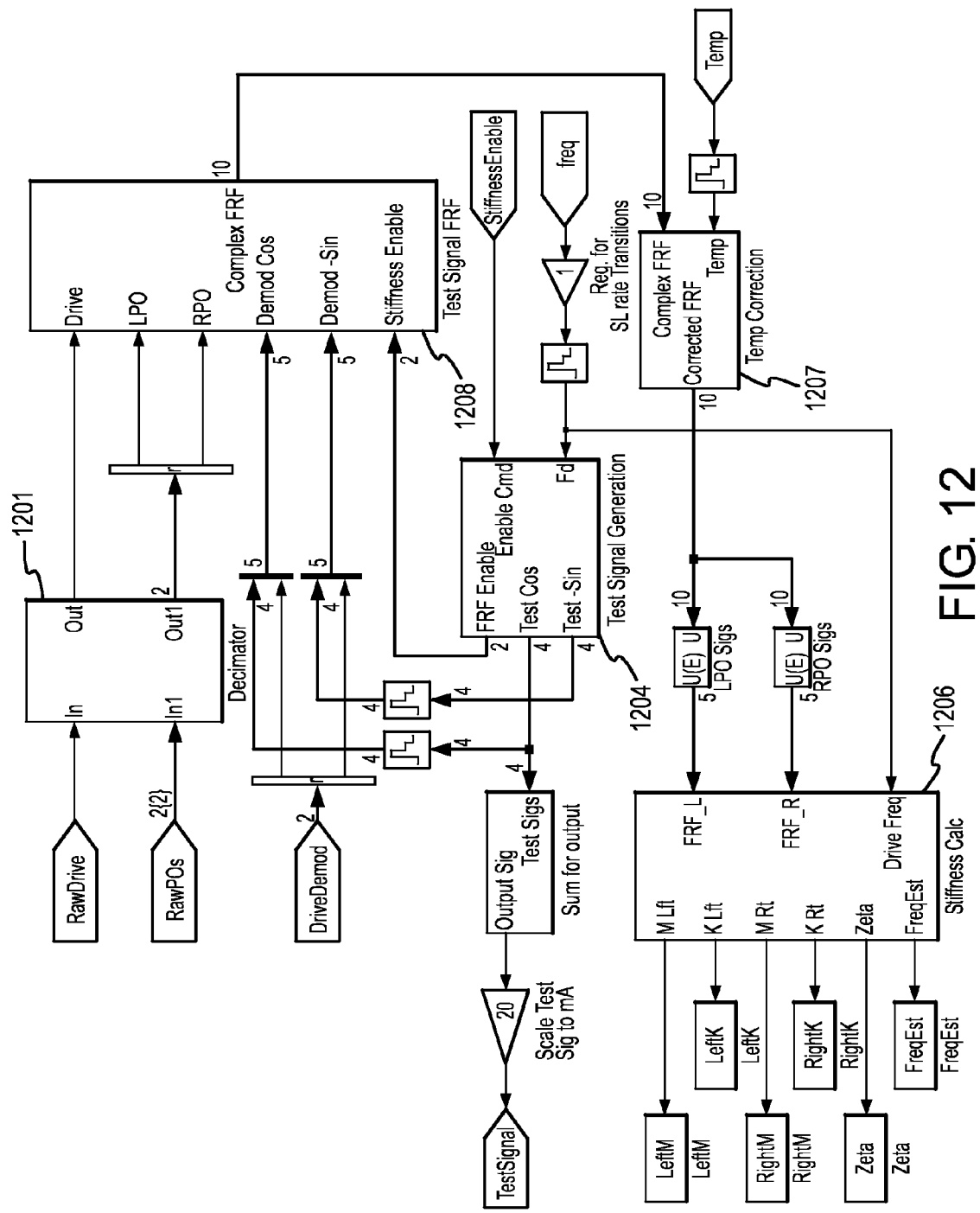
FIG. 12 shows the overall FRF-based stiffness estimation system according to an embodiment of the invention.

FIG. 12 shows the overall FRF-based stiffness estimation system according to an embodiment of the invention. There are six distinct inputs to the system, indicated by pentagons that are signal sources (three on the upper left and three on the lower right). The "RawDrive" and "RawPOs" inputs are the raw readings from the pickoffs and the drive current. These are down sampled to 2 kHz by the Decimator block 1201 and then fed into the FRF coefficient estimation subsystem. The "DriveDemod" input is a sine and cosine signal at the drive frequency that is taken from a digital drive system. These signals are combined with sinusoids generated at the test frequencies and fed into the FRF coefficient estimation subsystem as bases for demodulation. The "StiffnessEnable" estimate is a logical input, allowing the digital drive system to control when the stiffness estimation algorithm is active. The "freq" input is the drive frequency, as estimated by the digital drive system. It is input to the test signal generation block 1204 and the stiffness calculation block 1206. The "Temp" input is the temperature read from the flow meter that is inputted into the temperature correction block 1207. The FRF stiffness estimation algorithm outputs the system parameter estimates, as well as the "TestSignal" output at the far left side of the diagram. This test signal output contains excitation at the four test frequencies that are to be added to the driver command.

These inputs and outputs form the bulk of the interface to the digital drive. The test signals are added to the drive command immediately before output to a driver device. In order to make this FCF validation procedure transparent to the drive system, it is necessary to remove the test signals from the pickoffs. This is done in one embodiment with a set of notch filters tuned to the exact frequencies of the test signals.

The Test Signal FRF block 1208 of FIG. 11 performs demodulations. The pickoff and drive signals are demodulated at each of five input frequencies, the four generated test signal frequencies, and the drive frequency. After doing the complex demodulation using the sine and cosine bases, the real and imaginary components of each signal are decimated down to a lower frequency and low pass filtered to 0.4 Hz. It is necessary that these signals be uncontaminated in this region, as any spectral component within 0.4 Hz of the test signal will not be suppressed and will appear in the output. The complex coefficients for the pickoffs and drive current at each frequency are then used to estimate the FRF at that frequency. The power spectra are averaged over a number of samples, and the lower-rate FRF estimate is output.

The meter electronics and methods according to the invention can be employed according to any of the embodiments in order to provide several advantages, if desired. The invention provides a stiffness parameter (K) that is substantially related to a flowtube stiffness of the flow meter. The invention provides a stiffness parameter (K) that does not rely on stored or recalled calibration values for generation. The invention provides a stiffness parameter (K) that is obtained solely from a vibrational response of the flow meter. Likewise, the invention provides a mass parameter (M) and a damping parameter (C) from the vibrational response.

The invention provides a stiffness detection/calibration process without the need for a factory calibration process. The invention can perform a stiffness/FCF calibration process in the field. The invention can perform a stiffness/FCF calibration process at any time. The invention can perform a stiffness/FCF calibration process without the need for a calibration test rig and/or known flow materials. The invention can perform stiffness/FCF calibration processes that determine changes in stiffness of the flow meter over time.

We claim:

1. Meter electronics (20) for a flow meter (5), the meter electronics (20) comprising an interface (201) for receiving three or more vibrational responses from the flow meter (5), with the three or more vibrational responses including a substantially fundamental frequency response and two or more non-fundamental frequency responses, and a processing system (203) in communication with the interface (201), with the meter electronics (20) further comprising:

the processing system (203) being configured to receive the three or more vibrational responses from the interface (201), generate a pole-residue frequency response function from the three or more vibrational responses, with the pole-residue frequency response function comprising a first order pole-residue frequency response function comprising $H(\omega)=R/(j\omega-\lambda)+\overline{R}/(j\omega-\overline{\lambda})$, and determine at least a stiffness parameter (K) from the pole-residue frequency response function, wherein the stiffness parameter (K), the damping parameter (C), and the mass parameter (M) are determined according to the equations $M=1/2jR\omega_d$, $K=(\omega_n)^2 M$, and $C=2\zeta\omega_n M$, wherein the (R) term comprises a residue, the ($\overline{R}$) term comprises a complex conjugate of (R), the (λ) term comprises a pole, the ($\overline{\lambda}$) term comprises a complex conjugate of (λ), the (ξ) term comprises a decay characteristic, the (ω) term comprises a circular excitation frequency, the ($\omega_n$) term comprises a natural frequency, and the ($\omega_d$) term comprises a damped natural frequency.

2. The meter electronics (20) of claim 1, with the processing system (203) being further configured to determine a damping parameter (C) from the pole-residue frequency response function.

3. The meter electronics (20) of claim 1, with the processing system (203) being further configured to determine a mass parameter (M) from the pole-residue frequency response function.

4. The meter electronics (20) of claim 1, with the processing system (203) being further configured to compute the pole (λ), a left residue ($R_L$), and a right residue ($R_R$) from the pole-residue frequency response function.

5. The meter electronics (20) of claim 1, with the three or more vibrational responses comprising at least one tone above the fundamental frequency response and at least one tone below the fundamental frequency response.

6. The meter electronics (20) of claim 1, with the three or more vibrational responses comprising at least two tones above the fundamental frequency response and at least two tones below the fundamental frequency response.

7. The meter electronics (20) of claim 1, with the pole-residue frequency response function comprising a first order pole-residue frequency response function.

8. A method for determining a stiffness parameter (K) of a flow meter, the method comprising:
- meter electronics receiving three or more vibrational responses of the flow meter, with the three or more vibrational responses including a substantially fundamental frequency response and two or more non-fundamental frequency responses;
- the meter electronics generating a pole-residue frequency response function from the three or more vibrational responses, with the pole-residue frequency response function comprising a first order pole-residue frequency response function comprising $H(\omega)=R/(j\omega-\lambda)+\bar{R}/(j\omega-\bar{\lambda})$; and
- the meter electronics determining at least a stiffness parameter (K) from the pole-residue frequency response function, wherein the stiffness parameter (K), the damping parameter (C), and the mass parameter (M) are determined according to the equations $M=1/2jR\omega_d$, $K=(\omega_n)^2 M$, and $C=2\zeta\omega_n M$, wherein the (R) term comprises a residue, the ($\bar{R}$) term comprises a complex conjugate of (R), the ($\lambda$) term comprises a pole, the ($\bar{\lambda}$) term comprises a complex conjugate of ($\lambda$), the ($\xi$) term comprises a decay characteristic, the ($\omega$) term comprises a circular excitation frequency, the ($\omega_n$) term comprises a natural frequency, and the ($\omega_d$) term comprises a damped natural frequency.

9. The method of claim 8, further comprising the meter electronics determining a damping parameter (C) from the pole-residue frequency response function.

10. The method of claim 8, further comprising the meter electronics determining a mass parameter (M) from the pole-residue frequency response function.

11. The method of claim 8, further comprising the meter electronics computing the pole ($\lambda$), a left residue ($R_L$), and a right residue ($R_R$) from the pole-residue frequency response function.

12. The method of claim 8, with the three or more vibrational responses comprising at least one tone above the fundamental frequency response and at least one tone below the fundamental frequency response.

13. The method of claim 8, with the three or more vibrational responses comprising at least two tones above the fundamental frequency response and at least two tones below the fundamental frequency response.

14. The method of claim 8, with the pole-residue frequency response function comprising a first order pole-residue frequency response function.

15. The method of claim 8, further comprising;
- the meter electronics receiving a second set of three or more vibrational responses from the flow meter at a second time $t_2$;
- the meter electronics generating a second stiffness characteristic ($K_2$) from the second set of three or more vibrational responses;
- the meter electronics comparing the second stiffness characteristic ($K_2$) to the stiffness parameter (K); and
- the meter electronics detecting the stiffness change ($\Delta K$) if the second stiffness characteristic ($K_2$) differs from the stiffness parameter (K) by more than a predetermined tolerance.

16. The method of claim 15, further comprising the meter electronics detecting the stiffness change ($\Delta K$) if the second stiffness characteristic ($K_2$) differs from the stiffness parameter (K) by more than a predetermined stiffness tolerance.

17. The method of claim 15, further comprising the meter electronics quantifying the stiffness change (AK) from the comparing of K to $K_2$.

18. A method for determining a stiffness change ($\Delta K$) in a flow meter, the method comprising:
- meter electronics receiving three or more vibrational responses of the flow meter, with the three or more vibrational responses including a substantially fundamental frequency response and two or more non-fundamental frequency responses;
- the meter electronics generating a pole-residue frequency response function from the three or more vibrational responses, with the pole-residue frequency response function comprising a first order pole-residue frequency response function comprising $H(\omega)=R/(j\omega-\Delta)+\bar{R}/(j\omega-\bar{\lambda})$;
- the meter electronics determining at least a stiffness parameter (K) from the pole-residue frequency response function, wherein the stiffness parameter (K), the damping parameter (C), and the mass parameter (M) are determined according to the equations $M=1/2jR\omega_d$, $K=(\omega_n)^2 M$, and $C=2\zeta\omega_n M$, wherein the (R) term comprises a residue, the ($\bar{R}$) term comprises a complex conjugate of (R), the ($\lambda$) term comprises a pole, the ($\bar{\lambda}$) term comprises a complex conjugate of ($\lambda$), the ($\xi$) term comprises a decay characteristic, the ($\omega$) term comprises a circular excitation frequency, the ($\omega_n$) term comprises a natural frequency, and the ($\omega_d$) term comprises a damped natural frequency;
- the meter electronics receiving a second set of three or more vibrational responses from the flow meter at a second time $t_2$;
- the meter electronics generating a second stiffness characteristic ($K_2$) from the second set of three or more vibrational responses;
- the meter electronics comparing the second stiffness characteristic ($K_2$) to the stiffness parameter (K); and
- the meter electronics detecting the stiffness change ($\Delta K$) if the second stiffness characteristic ($K_2$) differs from the stiffness parameter (K) by more than a predetermined tolerance.

19. The method of claim 18, further comprising the meter electronics detecting the stiffness change ($\Delta K$) if the second stiffness characteristic ($K_2$) differs from the stiffness parameter (K) by more than a predetermined stiffness tolerance.

20. The method of claim 18, further comprising the meter electronics quantifying the stiffness change ($\Delta K$) from the comparing of K to $K_2$.

21. The method of claim 18, with the determining comprising the meter electronics further determining a damping parameter (C) from the pole-residue frequency response function.

22. The method of claim 18, with the determining comprising the meter electronics further determining a mass parameter (M) from the pole-residue frequency response function.

23. The method of claim 18, with the determining further comprising the meter electronics computing the pole ($\lambda$), a left residue ($R_L$), and a right residue ($R_R$) from the pole-residue frequency response function.

24. The method of claim 18, with the three or more vibrational responses comprising at least one tone above the fundamental frequency response and at least one tone below the fundamental frequency response.

25. The method of claim 18, with the three or more vibrational responses comprising at least two tones above the fundamental frequency response and at least two tones below the fundamental frequency response.

26. The method of claim 18, with the pole-residue frequency response function comprising a first order pole-residue frequency response function.

* * * * *